United States Patent
Collado Cano et al.

(10) Patent No.: US 6,504,052 B1
(45) Date of Patent: Jan. 7, 2003

(54) EXCITATORY AMINO ACID RECEPTOR MODULATORS

(75) Inventors: Ivan Collado Cano, Madrid (ES); Concepcion Pedregal Tercero, Madrid (ES); Alicia Marcos Llorente, Las Rozas (ES)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/979,437

(22) PCT Filed: May 26, 2000

(86) PCT No.: PCT/EP00/04896
§ 371 (c)(1),
(2), (4) Date: Nov. 16, 2001

(87) PCT Pub. No.: WO00/75102
PCT Pub. Date: Dec. 14, 2000

(30) Foreign Application Priority Data

Jun. 3, 1999 (EP) .............................. 99500089

(51) Int. Cl.[7] ........................ C07C 61/04; C07C 61/16; C07C 229/00; C07C 205/00; A01N 43/46
(52) U.S. Cl. ...................... 562/506; 562/433; 562/435; 562/441; 562/442; 562/444; 562/451; 562/456; 562/458; 514/217; 514/437
(58) Field of Search .................. 562/506, 433, 562/435, 441, 442, 444, 451, 456, 458; 514/217, 437

(56) References Cited

FOREIGN PATENT DOCUMENTS

| EP | 0 870 760 | 10/1998 |
|---|---|---|
| JP | 6-179643 | 6/1994 |
| JP | 08 301825 | 11/1996 |
| WO | WO 98 00391 | 5/1997 |
| WO | WO 97 19049 | 8/1998 |

OTHER PUBLICATIONS

Pellicciari, Roberto, et al.: Synthesis and Pharmacological Characterization of All Sixteen Steroisomers of 2–(2'–Carboxy–3'–phenylcyclopropyl)glycine, *J. Med. Chem.* 39(11), pp. 2259–2269 (1996); XP002122695.

Shimamoto, Keiko, et al.: "Syntheses and Conformation Analyses of Glutamate Analogs: 2–(2–Carboxy–3–substituted–cyclopropyl)glycines as Useful Probes for Excitatory Amino Acid Receptors," *J. Med. Chem.* 39(2), pp. 407–423, XP002122696 (1996).

Mazon, Angel, et al.: "Enantioselective Synthesis of 2–(3'–Alkyl–2'–Carboxy Cyclopropyl)Glycines," *Tetrahedron* 55, pp. 7057–7064 (1999).

Shimamoto, Keiko, et al.: "Synthesis of Trans–3'–substitued –CCG–IV Analogs and Their Characterization to Ionotropic Glutamate Receptors," *Bioorg. Med. Chem. Lett.* 6(20), pp. 10–22 (1996).

Shimamoto, Keiko, et al.: "Synthesis of Four Diastereomeric L–2–(Carboxycyclopropyl)glycines. Conformationally Constrined L–Glutamate Analogues," *J. Org. Chem.* 56, pp. 4167–4176 (1991).

Wilsch, Volker W., et al.: "Metabotopic Glutamate Receptor Agonist DCG–IV as NMDA Receptor Agonist in Inmature Rat Hippocampal Neurons," *Eur. J. Pharmacol.* 262, pp. 287–291 (1994).

U.S. patent application Ser. No. 09/979,322, Excitatory Amino Acid Receptor Modulators, filed Nov. 16, 2001.

Pellicciari et al, J. Med. Chem., 1996, vol. 39, pp. 2259–2269.*

* cited by examiner

Primary Examiner—Alan L. Rotman
Assistant Examiner—Hector M Reyes
(74) Attorney, Agent, or Firm—Arvie J. Anderson

(57) ABSTRACT

Compounds of the formula (I) in which $R^1$ is $C_{1-10}$ allyl; $C_{2-10}$ alkenyl; $C_{2-10}$ alkynyl; phenyl-$C_{2-10}$ alkyl or phenyl-$C_{2-10}$ alkenyl; and salts and esters thereof, modulate metabotropic glutamate receptor function and are useful in treating disorders of the central nervous system

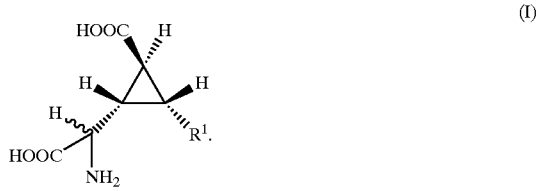

(I)

9 Claims, No Drawings

EXCITATORY AMINO ACID RECEPTOR MODULATORS

This application is a U. S. national phase entry, prudent to 35 USC 371, of PCT/EP00/04896, filed May 26, 2000 and published on Dec. 14, 2000, International Publication No. WO 00/75102, which claims the benefit of European Application No. 99500089.0 filed Jun. 3, 1999.

In the mammalian central nervous system (CNS), the transmission of nerve impulses is controlled by the interaction between a neurotransmitter, that is released by a sending neuron, and a surface receptor on a receiving neuron, which causes excitation of this receiving neuron. L-Glutamate, which is the most abundant neurotransmitter in the CNS, mediates the major excitatory pathway in mammals, and is referred to as an excitatory amino acid (EAA) The receptors that respond to glutamate are called excitatory amine acid receptors (EAA receptors). See Watkins & Evans, *Ann. Rev. Pharmacol. Toxicol.*, 21, 165 (1981); Monaghan, Bridges, and Cotman, *Ann. Rev. Pharmacol. Toxicol.*, 29, 365 (1989); Watkins, Krogsgaard-Larsen, and Honore, *Trans. Pharm. Sci.*, 11, 25 (1990). The excitatory amino acids are of great physiological importance, playing a role in a variety of physiological processes, such as long-term potentiation (learning and memory), the development of synaptic plasticity, motor control, respiration, cardiovascular regulation, and sensory perception.

Excitatory amino acid receptors are classified into two general. types. Receptors that are directly coupled to the opening of cation channels in the cell membrane of the neurons are termed "ionotropic". This type of receptor has been subdivided into at least three subtypes, which are defined by the depolarizing actions of the selective agonists N-methyl-D-aspartate (NMDA), alpha-amino-3-hydroxy-5-methylisoxazole-4-propionic acid (AMPA), and kainic acid (KA). The second general type of receptor is the G-protein or second messenger-linked "metabotropic" excitatory amino acid receptor. This second type is coupled to multiple second messenger systems that lead to enhanced phosphoinositide hydrolysis, activation of phospholipase D or C, increases or decreases in c-AMP formation, and changes in ion channel function. Schoepp and Conn, *Trends in Pharmacol. Sci.*, 14, 13 (1993). Both types of receptors appear not only to mediate normal synaptic transmission along excitatory pathways, but also participate in the modification of synaptic connections during development and throughout life. Schoepp, Bockaert, and Sladeczek, *Trends in Pharmacol. Sci.*, 11, 508 (1990); McDonald and Johnson, *Brain Research Reviews*, 15, 41 (1990).

The excessive or inappropriate stimulation of excitatory amino acid receptors leads to neuronal cell damage or loss by way of a mechanism known as excitotoxicity. This process has been suggested to mediate neuronal degeneration in a variety of conditions. The medical consequences of such neuronal degeneration makes the abatement of these degenerative neurological processes an important therapeutic goal.

The metabotropic glutamate receptors are a highly heterogeneous family of glutamate receptors that are linked to multiple second-messenger pathways. These receptors function to modulate the presynaptic release of glutamate, and the postsynaptic sensitivity of the neuronal cell to glutamate excitation. Compounds which modulate the function of these receptors, in particular agonists and antagonists of glutamate, are useful for the treatment of acute and chronic neurodegenerative conditions, and as antipsychotic, anticonvulsant, analgesic, anxiolytic, antidepressant, and anti-emetic agents.

Pellicciari et al., J. Med. Chem., 1996, 39, 2259–2269 refers to compounds known as metabotropic glutamate receptor agonists, in particular (2S,1'S,2'S)-2-(2-carboxycyclopropyl)glycine, also known as L-CCG-I; (2S,1'S,2'R,3'R)-2-(2'-carboxy-3'-(methoxymethyl)cyclopropylglycine, also known as cis-MCG-I; (2S,1'S,2'R,3'S)-2-(2'-carboxy-3'-(methoxymethyl)cyclopropylglycine, also known as trans-MCG-I; and (2S,1'R,2'R,3'R)-2-(2',3'-dicarboxycyclopropyl)glycine, also known as DCG-IV. The paper also describes the synthesis of the sixteen possible stereoisomers of 2-(2'-carboxy-3'-phenylcyclopropyl) glycine and their evaluation as excitatory amino acid receptor ligands. The compound (2S,1'S,2'S,3'R)-2-(2'-carboxy-3'-phenylcyclopropyl)glycine, also known as PCCG 4 is reported to be a metabotropic glutamate receptor antagonist.

Japanese patent application publication number JP 06179643 discloses MCG and generically discloses (2S,1'S,2'R)-2-(2-carboxy-3-alkoxymethyl- and 3-aralkoxymethyl-cyclopropyl)glycines as glutamate receptor agonists.

International patent application publication number WO 97/19049 discloses PCCG 4 and also generically discloses various 2-carboxy-3-arylcyclopropylglycines having affinity for metabotropic glutamate receptors.

International patent application publication number WO 98/00391 discloses 2-carboxy-3,3-dihalocyclopropylglycines, including (2S,1'S,2'S)-2-(2-carboxy-3,3-difluoro)-cyclopropylglycine as metabotropic glutamate receptor agonists.

European patent application, publication number EP-A1-0870760 discloses that certain 3-substituted 2-carboxycyclopropyl glycine derivatives are modulators of metabotropic glutamate receptor function. The preferred compounds are said to be those in which the substituents at the 1 and 2 positions are in a trans relationship. The examples illustrate such compounds in which the substituents at the 1 and 3 positions are also in a trans relationship. One such compound is (2S,1'S,2'S,3'S)-2'-carboxy-3'-methylcyclopropylglycine.

Surprisingly, novel 3-substituted 2-carboxycyclopropyl glycine derivatives having the substituents at the 1 and 2 positions in a trans relationship, and those at the 1 and 3 positions in a cis relationship, have now been found which are potent agonists of glutamate at metabotropic glutamate receptors.

Accordingly, the present invention provides a compound of the formula:

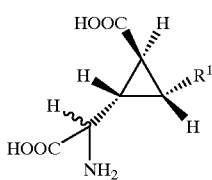

I in which $R^1$ is $C_{1-10}$ alkyl; $C_{2-10}$ alkenyl; $C_{2-10}$ alkynyl; phenyl-$C_{2-10}$ alkyl or phenyl-$C_{2-10}$ alkenyl; or a salt or ester thereof.

Compounds of the invention have been found to be agonists of glutamate at metabotropic glutamate receptors and are therefore useful in the treatment of disorders of the central nervous system such as neurological diseases, for example neurodegenerative diseases, and as antipsychotic, anxiolytic, drug-withdrawal, antidepressant, anticonvulsant, analgesic and anti-emetic agents.

It will be appreciated that the compounds of formula (I) contain at least four asymmetric carbon atoms, three being in the cyclopropane ring and one being at the α-carbon of the amino acid group. Accordingly, the compounds of the invention may exist in and be isolated in enantiomerically pure form, in racemic form, or in a diastereoisomeric mixture.

The amino acid moiety preferably has the natural amino configuration. Accordingly, preferred compounds according to the invention are those of the formula:

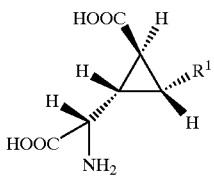

In the above general formulae, a $C_{1-10}$ alkyl group includes a $C_{1-4}$ alkyl group and can be straight or branched chain, such as, for example, methyl, ethyl, propyl, isopropyl, butyl and isobutyl, and is preferably methyl or ethyl. A $C_{2-10}$ alkenyl group includes, for example, vinyl, prop-2-enyl, but-3-enyl, pent-4-enyl and isopropenyl, and an alkenyl group can contain more than one double bond and, in addition, one or more triple bonds. A preferred alkenyl group is of the formula $R'—CH=CH—(CH_2)_r—$ where $R'$ is hydrogen or $C_{1-4}$ alkyl and r is 0, 1 or 2. A $C_{2-10}$ alkynyl group includes, for example, prop-2-ynyl, but-3-ynyl, pent-4-ynyl and oct-7-ynyl, and is preferably of the formula $R''C=C—(CH_2)_s—$ where $R''$ is hydrogen or $C_{1-4}$ alkyl and s is 0, 1 or 2.

Included within the group of compounds of formula I are those compounds in which $R^1$ is $C_{1-10}$ alkyl; $C_{2-10}$ alkenyl or $C_{2-10}$ alkynyl.

Examples of particular values for $R^1$ are:

for a $C_{1-10}$ alkyl group: methyl, ethyl, propyl and isopropyl;

for a $C_{2-10}$ alkenyl group: vinyl; prop-2-enyl and isopropenyl;

for a $C_{2-10}$ alkynyl group: propynyl;

for a phenyl-$C_{2-10}$ alkyl group: 2-phenylethyl; and for a phenyl-$C_{2-10}$ alkenyl group: 2-phenylvinyl.

Preferably $R^1$ is selected from methyl, ethyl, propyl, isopropyl, vinyl, prop-2-enyl, isopropenyl and propynyl.

Especially preferred are compounds in which $R^1$ is methyl or vinyl.

Particularly preferred compounds are:

(2S,1'S,2'S,3'R)-2-(3'-methyl-2'-carboxycyclopropyl)-glycine;

(2S,1's, 2'S,3'R)-2-[3'-(2"-ethyl)-2'-carboxycyclopropyl] glycine;

(2S,1'S,2'S,3'R)-2-[3'-(3"-propyl)-2'-carboxycyclopropyl] glycine;

(2SR,1'SR,2'SR,3'RS)-2-(3'-vinyl-2'-carboxycyclopropyl)-glycine; and (2S,1'S,2'S,3'R)-2-[3'-(2"-phenylethyl)-2'carboxycyclopropyl]glycine;

and pharmaceutically acceptable salts and esters thereof.

The present invention includes salts of the formula (I) compounds. These salts can exist in conjunction with the acidic or basic portion of the molecule and can exist as acid addition, primary, secondary, tertiary, or quaternary ammonium, alkali metal, or alkaline earth metal salts. Generally, the acid addition salts are prepared by the reaction of an acid with a compound of formula (I). The alkali metal and alkaline earth metal salts are generally prepared by the reaction of the hydroxide form of the desired metal salt with a compound of formula (I).

The salts of the compounds of formula I may be pharmaceutically-acceptable salts. However, other salts are included in the invention. They may serve as intermediates in the purification of compounds or in the preparation of other, for example pharmaceutically-acceptable, acid addition salts, or are useful for identification, characterisation or purification.

Acid addition salts are preferably the pharmaceutically acceptable, non-toxic addition salts with suitable acids, such as those with inorganic acids, for example hydrochloric, hydrobromic, nitric, sulphuric or phosphoric acids, or with organic acids, such as organic carboxylic acids, for example, glycollic, maleic, hydroxymaleic, fumaric, malic, tartaric, citric, salicyclic, o-acetoxybenzoic, or organic sulphonic, 2-hydroxyethane sulphonic, toluene-p-sulphonic, or naphthalene-2-sulphonic acid.

The present invention includes esters of the formula (I) compounds, such esters being for example aliphatic esters such as alkyl esters.

The esters of the compounds of formula I may be pharmaceutically acceptable metabolically labile esters of compounds of formula I. These are ester derivatives of compounds of formula I that are hydrolyzed in vivo to afford said compound of formula I and a pharmaceutically acceptable alcohol. Examples of metabolically labile esters include esters formed with (1–6C) alkanols in which the alkanol moiety may be optionally substituted by a (1–8C) alkoxy group, for example methanol, ethanol, propanol and methoxyethanol. The most preferred esters are alkyl esters derived from $C_{1-4}$ alkanols, especially methyl and ethyl esters.

The invention also comprises a process for preparing a compound according to formula (I), or a salt or ester thereof, which comprises:

(a) deprotecting a compound of formula

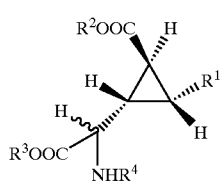

II in which $R^2$ and $R^3$ each independently represents hydrogen or a carboxyl protecting group, and $R^4$ represents hydrogen or an amine protecting group;

(b) hydrolysing a compound of formula

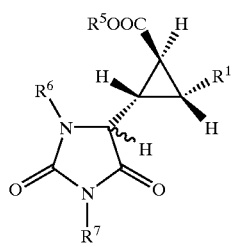

III in which $R^5$ represents a hydrogen atom or a carboxyl protecting group, and $R^6$ and $R^7$ each independently represents a hydrogen atom, a $C_{1-4}$ alkyl group, a phenyl $C_{1-4}$ alkyl group in which the phenyl group is unsubstituted or substituted by halo, $C_{1-4}$ alkyl or $C_{1-4}$ alkoxy, or $C_{3-4}$ alkenyl; or (c) hydrolysing a compound of formula

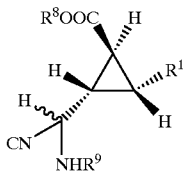

IV in which $R^1$ represents a hydrogen atom or a carboxy protecting group, and $R^9$ represents a hydrogen atom or an amine protecting group;

followed when necessary by recovering a diastereomer or isomer of the compound, or forming a salt or ester thereof.

The protection of carboxylic acid groups is described in McOmie, Protecting Groups in Organic Chemistry, Plenum Press, NY, 1973, and Greene and Wuts, Protecting Groups in Organic Synthesis, 2nd. Ed., John Wiley & Sons, NY, 1991. Examples of carboxy protecting groups include $C_1$–$C_6$ alkyl groups such as methyl, ethyl, t-butyl and t-amyl; aryl ($C_1$–$C_4$)alkyl groups such as benzyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, benzhydryl and trityl; silyl groups such as trimethylsilyl and t-butyldimethylsilyl; and allyl groups such as allyl and 1-(trimethylsilylmethyl)prop-1-en-3-yl.

Examples of amine protecting groups include acyl groups, such as groups of formula $R^{10}CO$ in which $R^{10}$ represents $C_{1-6}$ alkyl, $C_{3-10}$ cycloalkyl, phenyl $C_{1-6}$ alkyl, phenyl, $C_{1-6}$ alkoxy, phenyl $C_{1-6}$ alkoxy, or a $C_{3-10}$ cycloalkoxy, wherein a phenyl group may be optionally substituted, for example by one or two of halogen, $C_1$–$C_4$ alkyl and $C_1$–$C_4$ alkoxy. Preferred amino protecting groups include t-butoxycarbonyl (Boc) and benzyl.

Examples of particular values for $R^2$, $R^3$, $R^5$ and $R^8$ are hydrogen, methyl, ethyl, n-propyl, n-butyl, t-butyl, benzyl, 4-methoxybenzyl, phenylethyl and phenylpropyl.

Examples of particular values for $R^4$ and $R^9$ include acetyl and tert-butoxycarbonyl.

Examples of particular values for $R^6$ and $R^7$ are hydrogen and benzyl.

The compounds of formula (II) may be deprotected by conventional methods. Thus, an alkyl carboxyl protecting group may be removed by hydrolysis. The hydrolysis may conveniently be performed by heating the compound of formula (II) in the presence of either a base, for example an alkali metal hydroxide such as lithium, sodium or potassium hydroxide, or an alkaline metal hydroxide, such as barium hydroxide or an acid such as hydrochloric acid. The hydrolysis is conveniently performed at a temperature in the range of from 20° C to 300° C. An aralkyl carboxyl protecting group may conveniently be removed by hydrogenation. The hydrogenation may be effected by reacting the compound of formula (II) with hydrogen in the presence of a Group VIII metal catalyst, for example a palladium catalyst such as palladium on charcoal. Suitable solvents for the reaction include alcohols such as ethanol. The reaction is conveniently performed at a temperature in the range of from 0° C. to 100° C.

An acyl, amine protecting group is also conveniently removed by hydrolysis, for example as described for the removal of an alkyl carboxyl protecting group. Thus, a tert-butoxycarbonyl, amine protecting group may conveniently be removed in the presence of an acid, for example hydrochloric acid or trifluoroacetic acid. The hydrolysis is performed in the presence of a solvent such as water, ethyl acetate or dichloromethane and at a temperature in the range of from 20° C. to 100° C.

The compounds of formula III are conveniently hydrolyzed in the presence of a base, for example an alkali metal hydroxide such as lithium, sodium or potassium hydroxide, or an alkaline earth metal hydroxide such as barium hydroxide. Suitable reaction media include water. The temperature is conveniently in the range of from 50° C. to 150° C.

The compounds of formula IV are conveniently hydrolyzed in the presence of an acid, such as hydrochloric acid or sulfuric acid, or a base, such as an alkali metal hydroxide, for example sodium hydroxide. The hydrolysis is conveniently performed in an aqueous solvent such as water, or in an alkanol such as methanol or ethanol, and at a temperature in the range of from 20° C. to 200° C.

Compounds of formula (II) may be prepared by a procedure analogous to that described in Ohfune Y., et al., J. Med. Chem., 1996, 39, 407–423. Thus they may be prepared by reacting a compound of formula

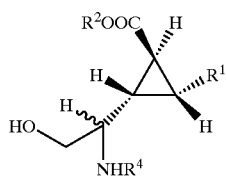

V with an oxidising agent. Convenient oxidising agents include Jones Reagent.

Compounds of formula (V) may be prepared by reacting a compound of formula

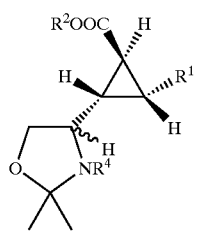

VI with a sulfonic acid, such as camphorsulfonic acid (CSA) and an alkanol, such as methanol.

Compounds of formula (VI) may be prepared by reacting a compound of formula

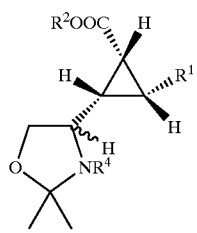

VII with a strong base, such as potassium hexamethyldisilane.

Compounds of formula (VII) may be prepared by reacting a compound of formula

VIII

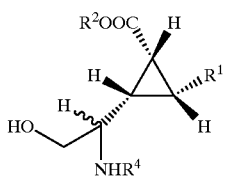

with acetone dimethyl ketal in the presence of a sulfonic acid, such as camphorsulfonic acid.

Compounds of formula VIII may be prepared by selectively deprotecting a compound of formula

IX

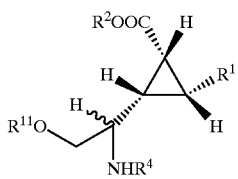

in which $R^{11}$ represents a hydroxyl protecting group, such as a tert-butyldimethylsilyl (TBS) group. A convenient reagent for removing a TBS group is camphorsulfonic acid in methanol.

The compounds of formula (IX) may be prepared by reacting a compound of formula

X

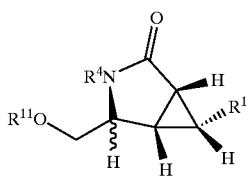

with a base, such as lithium hydroxide, for example in tetrahydrofuran, followed by introduction of the protecting group $R^2$, for example by treatment with diazomethane (to afford a compound in which $R^2$ is methyl).

Compounds of formula (X) may be prepared by treating a compound of formula

XI

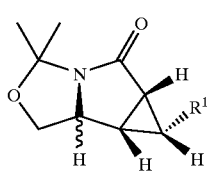

with an ion exchange resin, such as DOWEX 50Wx8, followed by introduction of the protecting groups $R^4$ and $R^{11}$, for example by stepwise reaction with tributylsilyl chloride in the presence of imidazole, followed by $Boc_2O$ in the presence of triethylamine and 4 dimethylaminopyridine.

Compounds of formula (XI) may be prepared by reacting a compound of formula

XII

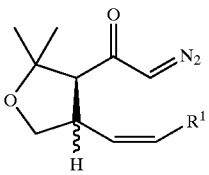

with palladium(II)acetate.

Compounds of formula (XII) may be prepared by diazotizing a compound of formula

XIII

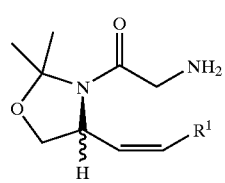

for example by reaction with sodium nitrite.

Compounds of formula (XIII) may be prepared by selectively deprotecting a compound of formula

XIV

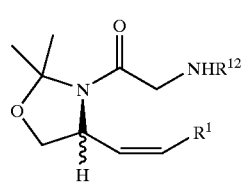

in which $R^{12}$ represents an amine protecting group, such as t-butoxycarbonyl. For example a t-butoxycarbonyl (Boc) group may conveniently be removed by treatment with trimethylsilyl trifluoromethanesulfonate (TMSOTf) and 2,6-lutidine.

The compounds of formula (XIV) may be prepared by reacting a compound of formula

XV

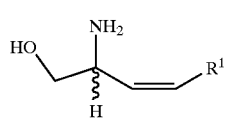

with an N-protected glycinate, such as N-hydroxysuccinimide N-(tert-butoxycarbonyl)glycinate, followed by reaction with acetone dimethylketal in the presence of a sulfonic acid such as p-toluenesulfonic acid.

The compounds of formula (XV) may be prepared by reacting a compound of formula

XVI

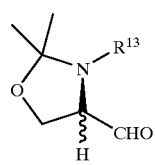

in which $R^{13}$ represents an amine protecting group, such as t-butoxycarbonyl, with a triphenylphosphine halide of formula $Ph_3P^+CH_2R^1 \ A^-$, in which $A^-$ represents a halide ion such as bromide, in the presence of a strong base, such as potassium hexamethyldisilane, followed by removal of the amine protecting group, and hydrolysis of the acetonide, for example by reaction with methanolic HCl.

Compounds of formula (II) may also be prepared by reacting a compound of formula

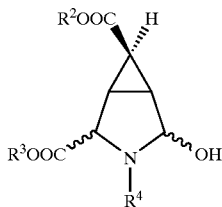

XVII with a Wittig reagent. For example, the compound of formula (XVII) may be reacted with an alkyl triphenylphosphonium bromide, such as methyl triphenylphosphonium bromide to afford a compound of formula (II) in which $R^1$ represents an alkenyl group, such as vinyl. The resultant product may then, if desired, be converted into another compound of formula (II), for example by catalytic hydrogenation to convert an alkenyl group to an alkyl group.

Compounds of formula (XVII) may be prepared by Swern oxidation of a compound of formula

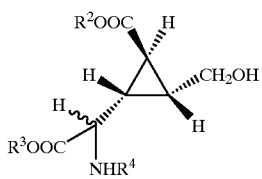

XVIII

The compounds of formula XVIII may be prepared either by hydrolysing a compound of formula XIX

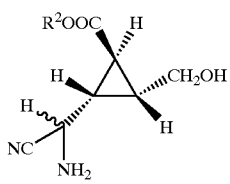

XIX for example using HCl in aqueous ethanol, followed by protecting the amino group, for example by reaction with $Boc_2O$ in tetrahydrofuran or dioxane in the presence of $NaHCO_3$,
or by hydrolysing a compound of formula XX

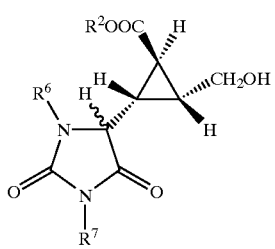

XX in the presence of a base, for example sodium hydroxide, in an aqueous solution at an elevated temperature, for example about 100° C., followed by protecting the carboxylic acid groups, for example using HCl in anhydrous ethanol, and protecting the amino group, for example by reaction with $Boc_2O$ in tetrahydrofuran or dioxane in the presence of $NaHCO_3$.

The compounds of formula XIX may be prepared by reacting a compound of formula XXI

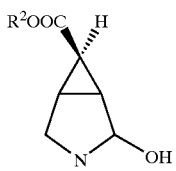

XXI with ammonium chloride and potassium cyanide in the presence of aluminium oxide. A convenient solvent is acetonitrile.

The compounds of formula XX may be prepared by hydrolysing a compound of formula XXI with an alkali metal hydroxide, for example using sodium hydroxide in aqueous ethanol, followed by treatment with an alkali metal cyanide, such as lithium, sodium or potassium cyanide, and ammonium carbonate in an aqueous alcohol, such as aqueous ethanol. Conveniently the reaction is performed at a temperature of from 35° C. to 150° C.

Compounds of formula XXI may be prepared by oxidising a compound of formula XXII

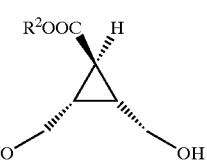

XXII for example by employing a Swern oxidation.

Compounds of formula XXII may be prepared by reacting a compound of formula

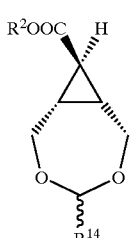

XXIII in which $R^{14}$ represents a hydrogen atom, a $C_{1-4}$ alkyl group or a phenyl group, with HCl or camphorsulphonic acid in an alkanol such as ethanol.

Compounds of formula XXIII may be prepared by reacting a compound of formula

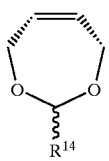

XXIV with N$_2$CHCO$_2$R$^2$ in the presence of Rh$_2$(OAc)$_4$. A convenient solvent is pentane.

The compounds of formula (III) may be prepared by reacting a compound of formula

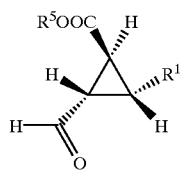

XXV with an alkali metal cyanide, such as lithium, sodium or potassium cyanide, and ammonium carbonate in an aqueous alcohol, such as aqueous ethanol. Conveniently the reaction is performed at a temperature of from 35° C. to 150° C. If desired, the compounds of formula (III) may then be alkylated, for example using a compound of formula R$^6$Cl or R$^7$Cl. The alkylated compounds are readily separated into their diastereomers.

Compounds of formula (IV) may be prepared by reacting a compound of formula (XXV), in which R$^8$ is as defined for R$^5$, with an alkali metal cyanide, such as lithium, sodium or potassium cyanide, and an ammonium halide, such as ammonium chloride. It has been found advantageous to perform the reaction in the presence of ultrasound. Thus, the ammonium halide and alkali metal cyanide are advantageously mixed with chromatography grade alumina in the presence of a suitable diluent, such as acetonitrile. The mixture is then irradiated with ultrasound, whereafter the compound of formula XXV is added, and the mixture is again irradiated.

The resultant mixture of diastereoisomeric aminonitriles may then be reacted with an acylating agent, such as acetyl chloride in the presence of a suitable base, for example an amine such as diisopropylamine, and in the presence of a suitable solvent such as dichloromethane, to afford a mixture of diastereomeric acylaminonitriles. The desired stereoisomer may conveniently be separated from this mixture, for example by chromatography.

Alternatively, compounds of formula (IV) may be prepared by reacting a compound of formula (XXV) with a chiral 2-arylglycinol, such as (R)-2-phenylglycinol, followed by trimethylsilylcyanide. The reaction is conveniently conducted in the presence of a solvent such as methanol. The product of the reaction is a mixture of diastereomers corresponding with formula (IV) in which R$^9$ represents a 1-aryl-2-hydroxyethyl group. The desired diastereomer may be isolated from the mixture, for example by chromatography, and then reacted with an oxidising agent such as lead tetraacetate to afford a compound of formula (IV).

The compounds of formula (XXV) may be prepared by oxidising a compound of formula

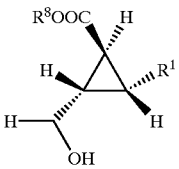

XXVI for example by a Swern oxidation, or by reaction with tetrapropylammonium perruthenate and N-methylmorpholine-N-oxide in the presence of a molecular sieve (4 Å).

The compounds of formula (XXVI) may be prepared by reacting a compound of formula (XXI) with a Wittig reagent of formula Ph$_3$P$^+$CH$_2$R$^{15}$ is A$^-$, in which A$^-$ represents a halide ion such as bromide and R$^{15}$ represents a hydrogen atom or an alkyl group, in the presence of a strong base, such as potassium hexamethyldisilane. Convenient solvents include ethers, such as dioxan. The resultant alkenyl compound may be reduced to afford an alkyl compound, for example by catalytic hydrogenation using palladium on charcoal as catalyst.

The compounds of formula (XXV) may alternatively be prepared by reacting a compound of formula (XXVII)

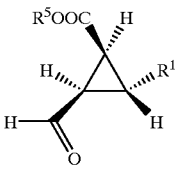

XXVII with an alkali metal hydroxide, such as sodium hydroxide, in an aqueous alcohol solvent, such as aqueous methanol, followed by diazomethane. The process affords a mixture. of a compound of. formula (XXVI) and a compound of formula (XXV), which may then be reacted with a chiral 2-arylglycinol and trimethylsilylcyanide as described hereinabove.

The compounds of formula XXVII may be prepared by reacting a compound of formula

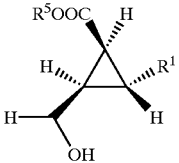

XXVIII for example by a Swern oxidation, or by reaction with tetrapropylammonium perruthenate and N-methylmorpholine-N-oxide in the presence of a molecular sieve (4 Å).

The compounds of formula (XXVIII) may be prepared by reacting a compound of formula

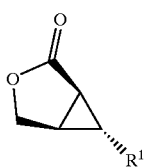
(XXIX)

with an alkali metal hydroxide, such as lithium hydroxide, to afford a compound of formula (XXVIII) in which $R^5$ represents hydrogen, followed by followed by introducing a protecting group $R^5$, for example by reaction with diazomethane to produce a compound in which $R^5$ is methyl.

The compounds of formula (XXIX) may be prepared by reacting a compound of formula

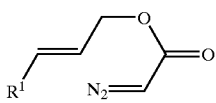
(XXX)

with dirhodium(II)tetrakis[methyl 2-pyrrolidone-5(R)-carboxylate].

The compounds of formula (XXX) may be prepared by reacting a compound of formula

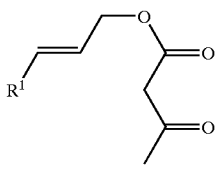
(XXXI)

with a sulfonyl azide such as p-acetamidobenzenesulfonyl azide in the presence of a base, such as triethylamine, followed by reaction with an aqueous alkali metal hydroxide, such as lithium hydroxide.

The compounds of formula (XXXI) may be prepared by reacting a compound of formula

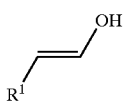
(XXXII)

with diketene in the presence of an alkali metal acetate, such as sodium acetate.

As described hereinabove, the compounds of the invention are useful for the treatment of disorders of the central nervous system.

According to another aspect therefore, the present invention provides a method of treating a patient suffering from or susceptible to a disorder of the central nervous system, which comprises administering an effective amount of a compound of formula I as defined hereinabove, or a pharmaceutically acceptable metabolically labile ester thereof, or a pharmaceutically acceptable salt thereof.

The particular effective amount or dose of compound administered according to this invention will of course be determined by the particular circumstances surrounding the case, including the compound administered, the route of administration, the particular condition being treated, and similar considerations. The compounds can be administered by a variety of routes including oral, rectal, transdermal, subcutaneous, intravenous, intramuscular, or intranasal routes. Alternatively, the compound may be administered by continuous infusion. A typical daily dose will contain from about 0.01 mg/kg to about 100 mg/kg of the active compound of this invention. Preferably, daily doses will be about 0.05 mg/kg to about 50 mg/kg, more preferably from about 0.1 mg/kg to about 25 mg/kg.

A variety of physiological functions have been shown to be subject to influence by excessive or inappropriate stimulation of excitatory amino acid transmission. The formula I compounds of the present invention are believed to have the ability to treat a variety of neurological disorders in patients associated with this condition, including acute neurological disorders such as cerebral deficits subsequent to cardiac bypass surgery and grafting, stroke, cerebral ischemia, spinal cord trauma, head trauma, perinatal hypoxia, cardiac arrest, and. hypoglycemic neuronal damage. The formula I compounds are believed to have the ability to treat a variety of chronic neurological disorders, such as Alzheimer's disease, Huntington's Chorea, amyotrophic lateral sclerosis, AIDS-induced dementia, ocular damage and retinopathy, cognitive disorders, and idiopathic and drug-induced Parkinson's. The present invention also provides methods for treating these disorders which comprises administering to a patient in need thereof an effective amount of a compound of formula I or a pharmaceutically acceptable metabolically labile ester thereof, or a pharmaceutically acceptable. salt thereof.

The formula I compounds of the present invention are also believed to have the ability to treat a variety of other neurological. disorders in patients that are associated with glutamate dysfunction, including muscular spasms, convulsions, migraine headaches, urinary incontinence, psychosis, (such as schizophrenia), drug tolerance and withdrawal (such as nicotine, opiates and benzodiazepines), anxiety and related disorders, emesis, brain edema, chronic pain, and tardive dyskinesia. The formula I compounds are also useful as antidepressant and analgesic agents. Therefore, the present invention also provides methods for treating these disorders which comprise administering to a patient in need thereof an effective amount of the compound of formula I, or a pharmaceutically acceptable metabolically labile ester thereof, or a pharmaceutically acceptable salt thereof.

The term "treating" for purposes of the present invention, includes prophylaxis, amelioration or elimination of a named condition once the condition has been established.

The term "patient" for purposes of the present invention is defined as any warm blooded animal such as, but not limited to, a mouse, guinea pig, dog, horse, or human. Preferably, the patient is human.

According to another aspect, the present invention provides a compound of formula I as defined hereinabove, or a pharmaceutically acceptable metabolically labile ester thereof, or a pharmaceutically acceptable salt thereof, for use as a pharmaceutical.

According to yet another aspect, the present invention provides the use of a compound of formula I as defined hereinabove, or a pharmaceutically acceptable metabolically labile ester thereof, or a pharmaceutically acceptable salt thereof, for the manufacture of a medicament for treating a disorder of the central nervous system.

The ability of compounds to modulate metabotropic glutamate receptor function may be demonstrated by examining their ability to influence either cAMP production (mGluR 2, 3, 4, 6, 7 or 8) or phosphoinositide hydrolysis (mGluR 1 or 5) in cells expressing these individual human metabotropic glutamate receptor (mGluR) subtypes. (D. D. Schoepp, et al., *Neuropharmacol.*, 1996, 35, 1661–1672 and 1997, 36, 111).

In these tests the compound of Example 1 of the present application was found to reverse [3 H] LY341495 binding with a Ki of 100.2 nM at mGluR2. In comparison, (2S,1'S, 2'S,3'S)-2'-carboxy-3'methylcyclopropylglycine, disclosed in EP-A-0870760 was found to reverse [3 H] LY341495 binding with a Ki of 2645 nM at mGluR2. (LY341495 is described in Ornstein et al., J. Med. Chem., 1998, 41, 346–357 and J. Med. Chem., 1998, 41, 358 to 378).

The compounds of the present invention are preferably formulated prior to administration. Therefore, another aspect of the present invention is a pharmaceutical formulation comprising a compound of formula I, a pharmaceutically acceptable metabolically labile ester thereof, or a pharmaceutically acceptable salt thereof, and a pharmaceutically-acceptable carrier, diluent, or excipient. The present pharmaceutical formulations are prepared by known procedures using well-known and readily available ingredients. In making the compositions of the present invention, the active ingredient will usually be mixed with a carrier, or diluted by a carrier, or enclosed within a carrier, and may be in the form of a capsule, sachet, paper, or other container. When the carrier serves as a diluent, it may be a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example, up to 10% by weight of active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum, acacia, calcium phosphate, alginates, tragacanth, gelatin, calcium silicate, microcrystalline cellulose, polyvinylpyrrolidone, cellulose, water syrup, methyl cellulose, methyl and propyl hydroxybenzoates, talc, magnesium stearate, and mineral oil. The formulations can additionally include lubricating agents, wetting agents, emulsifying and suspending agents, preserving agents, sweetening agents, or flavoring agents. Compositions of the invention may be formulated so as to provide quick, sustained, or delayed release of the active ingredient after administration to the patient by employing procedures well known in the art.

The compositions are preferably formulated in a unit dosage form, each dosage containing from about 5 mg to about 500 mg, more preferably about 25 mg to about 300 mg of the active ingredient. The term "unit dosage form" refers to a physically. discrete unit suitable as unitary dosages for human subjects and other mammals, each unit containing a predetermined quantity of active material calculated to produce the desired therapeutic effect, in association with a suitable pharmaceutical carrier, diluent, or excipient. The following formulation examples are illustrative only and are not intended to limit the scope of the invention in any way.

| Formulation 1 Hard gelatin capsules are prepared using the following ingredients: | |
|---|---|
| | Quantity (mg/capsule) |
| Active Ingredient | 250 |
| Starch, dried | 200 |
| Magnesium stearate | 10 |
| Total | 460 mg |

The above ingredients are mixed and filled into hard gelatin capsules in 460 mg quantities.

| Formulation 2 Tablets each containing 60 mg of active ingredient are made as follows: | |
|---|---|
| Active Ingredient | 60 mg |
| Starch | 45 mg |
| Microcrystalline cellulose | 35 mg |
| Polyvinylpyrrolidone | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

The following Examples illustrate the invention. In the Examples, the term "Garner's aldehyde" signifies 1,1-dimethylethyl (S) or (R)-4-formyl-2,2-dimethyl-3-oxazolidine carboxylate, $Ph_3PEtBr$ signifies (ethyl) triphenylphosphonium bromide, KHDMS and LiHDMS signify potassium and lithium hexamethyldisilazane. respectively, $Et_2O$ signifies diethylether, AcOEt signifies ethyl acetate, MeOH signifies methanol, Boc signifies t-butoxycarbonyl, $Et_3N$ signifies triethylamine, THF signifies tetrahydrofuran, TMSOTf signifies trimethylsilyl trifluoromethanesulfonate, $Pd(OAc)_2$ signifies palladium acetate, NMO signifies N-methylmorpholine-N-oxide, TPAP signifies tetrapropylammonium perruthenate, TMSCN signifies trimethylsilylcyanide, $Rh_2(5R-MEPY)_4$ signifies dirhodium(II)tetrakis[methyl 2-pyrrolidone-5(R)-carboxylate], DMF signifies dimethylformamide, DMAP signifies 4-dimethylaminopyridine, Jones Reagent signifies a solution of 1.0 g of $Na_2Cr_2O_7.2H_2O$ and 1.34 g of sulfuric acid in $H_2O$ (total volume 5 ml), DBU signifies 1,8-diazabicyclo[5.4.0]undec-7-ene and DME signifies ethylene glycol dimethyl ether.

EXAMPLE 1

(2S,1'S,2'S,3'R)-2-(3'-Methyl-2'-carboxycyclopropyl)glycine

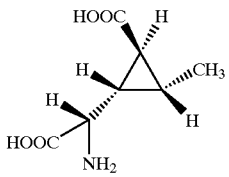

a) (4S)-3-N-(tert-Butoxycarbonyl)-4-[(1Z)-1-propenyl]-2,2-dimethyl-1,3-oxazolidine To a suspension of Ph$_3$PEtBr (4.86 g, 13.9 mmol) in anhydrous dioxane (100 mL) under nitrogen at room temperature, a 0.5 M solution of KHMDS in toluene (22.3 mL, 11.7 mmol) was added. After stirring for one hour, the mixture was added dropwise via cannula to a solution of the Garner's aldehyde (2.0 g, 8.7 mmol) in anhydrous dioxane (40 mL) under nitrogen at room temperature. After the addition was completed, the reaction mixture was stirred for 30 min and then poured onto a (1:1) mixture H$_2$O-Et$_2$O (500 mL). The layers were then separated and the aqueous layer was extracted with Et$_2$O (2×). The combined organic layers were dried (Na$_2$SO$_4$), filtered and evaporated to give a residue which was purified by chromatography using AcOEt/Hexane (1:10) as eluent to give 1.8 g (86% yield) of cis-olefin as the major isomer. $^1$H-NMR (300 MHz, CDCl$_3$): 1.44 (s, 9H), 1.52 (s, 3H), 1.60 (s, 3H), 1.70 (d, J=1.1 Hz, 3H), 3.65 (dd, J=3.3, 8.8 Hz, 1H), 4.06 (dd, J=6.0, 8.8 Hz, 1H), 4.72–4.62 (m, 1H) and 5.61–5.39 ppm (m, 2H).

b) (4S)-3-N-[(tert-Butoxycarbonyl)glycyl]-4-[(1Z)-1-propenyl]-2,2-dimethyl-1,3-oxazolidine To a solution of the product of step a) (1.77 g, 4.48 mmol) in MeOH (10 mL) at 0° C. was added 1N HCl/MeOH (30 mL) at 0° C. The reaction mixture was stirred at 0° C. for 1 hour and at room temperature overnight. The solvent was removed in vacuo and residue taken into H$_2$O (10 mL). This solution was adjusted to pH 7 by addition of 1N NaOH and then to pH 9 by Et$_3$N. The solvent was removed in vacuo and residue was dissolved in MeOH (20 mL) and THF (30 mL) (additional Et$_3$N was added until the solution became pH 9). To this solution at 0° C. was added N-hydroxysuccinimide N-(tert-butoxy-carbonyl)glycinate (2.2 g, 8.06 mmol) and then warmed to room temperature. After the mixture was stirred for 1 hour, the solvent was evaporated in vacuo and the oily residue was dissolved in AcOEt. The insoluble material was filtered off and filtrate concentrated in vacuo to give a residue which was subjected to column chromatography on silica gel (AcOEt). The resulting Boc-glycyl compound was dissolved in benzene (25 mL) and p-toluensulfonic acid (21 mg, 0.11 mmol) and 2,2-dimethoxypropane (1.9 mL, 15.4 mmol) were added. The mixture was stirred under reflux 24 hours. To this solution at room temperature, MeOH (5 mL) was added and mixture was stirred for 30 minutes. Then, NaHCO$_3$ (1–2 g) was added and, after stirring for 15 minutes, the insoluble material was filtered off. The filtrate was evaporated in vacuo and the residue purified by column chromatography (AcOEt/Hexane 1:5 and then 1:3) to give the Boc-glycyl acetonide (1.89 g, 86%). $^1$H-NMR (309 MHz, CDCl$_3$): 1.43 (s, 9H), 1.56 (s, 3H), 1.66 (s, 3H), 1.76 (dd, J=1.6, 7.2 Hz, 3H), 3.86–3.78 (m, 3H), 4.15 (dd, J=6.1, 8.8 Hz, 1H), 4.61–4.57 (m, 1H), 5.50–5.39 (m, 2H) and 5.74–5.63 ppm (m, 1H).

c) (1R,7S,8S,9R)-3-Aza-9-methyl-4,4-dimethyl-5-oxatricyclo[6.1.0.0$^{3,7}$]nonan-2-one To a solution of the product of step b) (2.7 g, 9.05 mmol) and 2,6-lutidine (3.27 mL, 28.06 mmol) in CH$_2$Cl$_2$ (30 mL) at room temperature under nitrogen was added TMSOTf (3.44 mL, 19.0 mmol). The mixture was stirred for 15 minutes and then cooled to 0° C. and quenched with saturated aqueous NH$_4$Cl solution (15 mL). The mixture was extracted with Et$_2$O, dried over Na$_2$SO$_4$ and the solvent was then evaporated in vacuo. The residue was taken into Et$_2$O (75 ml) at room temperature and a NaNO$_2$ (3.12 g, 45.25 mmol) solution in H$_2$O (35 ml) was added with intensive stirring. To this suspension, a 5% solution of citric acid in H$_2$O was added until the pH was adjusted to ~3. The mixture was vigorously stirred for 30 minutes at room temperature and then extracted three times with Et$_2$O. The combined organic layers were washed with NaHCO$_3$ and H$_2$O, dried over Na$_2$SO$_4$ and solvent was removed in vacuo. The resulting diazo ketone, without further purification was dissolved in benzene (200 mL) and Pd(OAC)$_2$ (100 mg, 0.45 mmol) was added. The mixture was heated at 70° C. for 30 minutes and then the solvent was evaporated in vacuo. The residue was purified by column chromatography using AcOEt/Hexane (1:2) as eluent to give the corresponding tricyclic compound (570 mg, 35%). $[\alpha]_D$=+57.0° (c=0.105, CHCl$_3$).
$^1$H-NMR (300 MHz, CDCl$_3$): 1.20 (d, J=6.6 Hz, 1H), 1.39 (s, 3H), 1.52–1.40 (m, 1H), 1.74 (s, 3H), 1.89 (dd, J=6.1, 8.2 Hz, 1H), 2.18–2.07 (m, 1H), 3.51 (dd, J=7.1, 9.9 Hz, 1H), 3.82–3.77 (m, 1H), 4.02 ppm (dd, J=5.5, 7.1 Hz, 1H). $^{13}$C-NMR (75 MHz, CDCl$_3$): 7.8, 17.3, 21.6, 23.8, 28.6, 28.9, 58.4, 67.9, 93.7 and 172.8 ppm.

d) (1R,4S,5S,6R)-3-Aza-3-N-(tert-butoxycarbonyl)-4[[(tert-butyldimethylsilyl)oxy]methyl]6-methylbicyclo[3.1.0]-hexane-2-one A mixture of the product of step c) (440 mg, 2.42 mmol) and Dowex 50Wx8 resin (H$^+$ form, 200 mg) in methanol (20 mL) was stirred overnight at room temperature. The resin was then filtered off, and the filtrate was concentrated in vacuo. To a solution of the residue and imidazole (660 mg, 9.68 mmol) in DMF (10 mL) was added a solution of tert-butyldimethylsilylchloride (1.10 g, 7.26 mmol) in DMF (5 mL). The reaction mixture was stirred overnight at room temperature and then poured onto cold water and extracted three times with Et$_2$O. The combined organic layers were dried over Na$_2$SO$_4$ and solvent removed in vacuo (DMF was removed by azeotropic distillation with toluene). A solution of the resulting residue, Et$_3$N (0.68 mL, 4.48 mmol), Boc$_2$O (790 mg, 3.63 mmol) and DMAP (60 mg, 0.48 mmol) in THF (15 mL) was stirred overnight at room temperature and then poured onto water and extracted three times with AcOEt. The combined organic layers were washed successively with 5% aqueous citric acid and water and dried over Na$_2$SO$_4$. The solvent was removed in vacuo and the resulting residue was purified by column chromatography (AcOEt/Hexane 1:6) to give the bicyclic lactone (640 mg, 75%). $^1$H-NMR (300 MHz, CDCl$_3$): 0.04 (s, 3H), 0.05 (s, 3H), 0.87 (s, 9H), 1.05 (d, J=6.6 Hz, 3H), 1.42–1.34 (m, 1H), 1.49 (s, 9H), 1.87 (dd, J=6.6, 7.7 Hz, 1H), 2.05–1.99 (m, 1H), 3.91–3.76 ppm (m, 3H). $^{13}$C-NMR (75 MHz, CDCl$_3$): −5.5 (2C), 7.6, 16.0, 18.1, 19.5, 25.7 (3C), 25.8, 28.0 (3C), 56.7, 63.7, 82.6, 149.5 and 172.4 ppm.

e) (1R,2S,3R,1'S)-2-[1'-[N-(tert-Butoxycarbonyl)amino]-2'-[(tert-butyldimethylsilyl)oxy]ethyl-3-methylcyclopropane-1-carboxylic Acid Methyl Ester.

To a solution of the product of step d) (480 mg, 1.35 mmol) in THF (13.5 mL), 1N LiOH (13.5 mL) was added.

The mixture was vigorously stirred overnight and then adjusted to pH~3 by addition of 5% aqueous citric acid. The aqueous layer was extracted three times with AcOEt, and the combined organic layers were dried over $Na_2SO_4$, filtered and the solvent removed in vacuo. A solution of the residue in $Et_2O$ (25 mL) at 0° C. was treated with a recently prepared $CH_2N_2$ solution in $Et_2O$ (until the yellow color is retained) at 0° C. After 30 minutes, the solvent was removed and the residue was purified by column chromatography (AcOEt/Hexane 1:6) to give the corresponding cyclopropane (380 mg, 73%).

$[\alpha]_D=-45.0°$ (c=0.132, $CHCl_3$). $^1$H-NMR (300 MHz, $CDCl_3$): 0.04 (s, 3H), 0.05 (s, 3H), 0.89 (s, 9H), 1.26–1.18 (m, 1H), 1.31 (d, J=6.6 Hz, 3H), 1.42 (s, 9H), 1.52–1.44 (m, 1H), 1.75–1.70 (m, 1H), 3.64 (s, 3H), 3.78–3.62 (m, 2H), 3.98–3.89 (m, 1H), 4.75 ppm (br s, 1H). $^{13}$C-NMR (75 MHz, $CDCl_3$): –5.5 (2C), 7.8, 18.3, 19.1, 20.2, 25.7, 25.8 (3C), 28.0 (3C), 47.4, 51.2, 65.1, 78.7, 154.8 and 171.8 ppm.

f) (4S,1'S,2'R,3'R)-3-N-(tert-Butoxycarbonyl)amino]-2,2-dimethyl-4-[2'-(methoxycarbonyl)-3'-methylcyclopropyl]-1,3-oxazilidone.

A mixture of cyclopropane (380 mg, 1.0 mmol) and camphorsulfonic acid (11.4 mg, 0.05 mmol) in MeOH (50 mL) was stirred at room temperature for 4 hours. The solvent was then removed in vacuo and the residue was taken into acetone. To this solution under nitrogen atmosphere 2,2-dimethoxypropane (1.2 mL, 9.8 mmol) was added, and the mixture was stirred for 2 hours at 60° C. Then, the reaction mixture was cooled to room temperature and $NaHCO_3$ (50 mg) was added. The mixture was then filtered the filtrate evaporated in vacuo. The residue was purified by column chromatography (AcOEt/Hexane 1:6) to give the corresponding acetonide (300 mg, 98%). $[\alpha]_D=-38.0°$ (c=0.105, $CHCl_3$).

$^1$H-NMR (300 MHz, $CDCl_3$): 1.27 (br s, 2H), 1.45 (br s, 15H), 1.60 (s, 3H), 1.87–1.81 (m, 1H), 3.71 (s, 3H), 3.85 (dd, J=2.2, 8.8 Hz, 1H), 4.07 (dd, J=6.0, 8.8 Hz, 1H), 4.37 ppm (br s, 1H). $^{13}$C-NMR (75 MHz, $CDCl_3$): 7.9, 16.6, 21.1, 24.5, 27.8, 27.9, 28.3 (3C), 51.0, 51.9, 68.6, 79.5, 93.4, 151.8 and 171.9 ppm.

g) (4S,1'S,2'S,3,R)-3-N-(tert-Butoxycarbonyl)amino]-2,2-dimethyl-4-[2'-(methoxycarbonyl)-3'-methylcyclopropyl]-1,3-oxazilidone.

To a solution of the product of step f) (300 mg, 0.96 mmol) in THF at –78° C. under nitrogen atmosphere, 0.5M KHMDS solution in toluene (5.75 mL, 2.87 mmol) was added. The mixture was slowly allowed to react at room temperature (over a period of 4 hours) and then stirred at room temperature for 15 minutes. The reaction mixture was cooled again to –78° C. and then quenched with a saturated $NH_4Cl$ aqueous solution. The aqueous layer was extracted twice with $Et_2O$ and AcOEt, and the combined organic layers were dried over $Na_2SO_4$ and evaporated in vacuo. The resulting residue was purified by column chromatography (AcOEt/Hexane 1:6) to give the epimerized product (250 mg, 83%). $[\alpha]_D=-15.4°$ (c=0.13, $CHCl_3$).

$^1$H-NMR (300 MHz, $CDCl_3$): 1.14 (d, J=6.1 Hz, 3H), 1.50 (br s, 15H), 1.75–1.57 (m, 3H), 3.66–3.57 (br s, 1H), 3.67 (s, 3H), 3.85 (d, J=8.2 Hz, 1H), 4.05–3.97 ppm (m, 1H). $^{13}$C-NMR (75 MHz, $CDCl_3$): 12.5, 19.8, 23.2, 27.0, 27.8, 28.3 (3C), 31.5, 51.4, 56.3, 68.6, 80.1, 94.0, 152.1 and 174.2 ppm.

h) (1S,2S,3R,1'S)-2-[1'-[N-(tert-Butoxycarbonyl)amino]-2'-hydroxyethyl-3-methylcyclopropane-1-carboxylic Acid Methyl Ester.

A mixture of the product of step g) (250 mg, 0.8 mmol) and camphorsulfonic acid (9.2 mg, 0.04 mmol) in MeOH (40 mL) was stirred at room temperature overnight. The following day, additional camphorsulfonic acid (11.0 mg, 0.047 mmol) was added and the mixture was stirred for 48 hours. Then, $NaHCO_3$ (50 mg) was added and the mixture was filtered off. The filtered was evaporated in vacuo and the residue was purified by column chromatography (AcOEt/Hexane 1:1) to give the corresponding alcohol (200 mg, 91%).

i) (2S,1'S,2'S,3'R)-2-(3'-Methyl-2'-carboxycyclopropyl) glycine.

To a solution of the product of step h) (200 mg, 0.73 mmol) in acetone (5 mL) at 0° C., Jones Reagent (1.12 mL) previously cooled to 0° C. was added. The mixture was stirred for 2 hours and 3 hours at room temperature. Then, the reaction was quenched with iso-propanol (5 mL) and $H_2O$ (5 mL), stirred for 15 minutes and poured onto AcOEt (75 mL). The organic layer was washed several times with H20, dried over $Na_2SO_4$. and evaporated in vacuo. The residue was dissolved in THF (5 mL) and 2.5N LiOH (10 mL) was added. The mixture was vigorously stirred overnight. The organic layer was separated and discarded and the aqueous layer washed with $Et_2O$. After the aqueous solution was adjusted to pH~1 by addition of 1N HCl at 0° C., it was extracted four times with AcOEt, and the combined organic layers were dried over $Na_2SO_4$ and evaporated in vacuo. A solution of the residue in 1N HCl/AcOEt (5 mL) was stirred overnight. The solvent was removed in vacuo and the resulting solid washed with $Et_2O$. The hydrochloride was dissolved in MeOH (3 mL) and propylene oxide (5 mL) was added. The mixture was stirred overnight and the resulting insoluble solid was filtered and washed with $Et_2O$ to give the title compound (75 mg, 60%). $^1$H-NMR (300 MHz, $D_2O$/KOD): 1.20–1.07 (m, 4H), 1.44–1.38 (m, 2H), 2.90 ppm (d, J=2.2, 9.8 Hz, 1H).

$^{13}$C-NMR (75 MHz, $D_2O$/KOD): 13.7, 21.9, 30.9, 32.8, 56.7, 183.4 and 184.5 ppm.

EXAMPLE 2

(2RS,1'SR,2'SR,3'RS)-2-(3'-Vinyl-2'carboxycyclopropyl)glycine

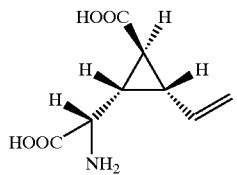

a) Ethyl 2,3-Dihydroxymethylcyclopropane Carboxylate.

To a solution of cis-4,7-dihydro-1,3-dioxepin (4.57 g, 45.6 mmol) in pentane (25 mL) under nitrogen at room temperature, $Rh_2(OAc)_4$ (220 mg, 0.5 mmol) was added. To the resulting suspension vigorously stirred, a solution of ethyl diazoacetate (10.5 mL, 100 mmol) in pentane (75 mL) was added dropwise at room temperature over a period of 3–4 hours. After the addition was completed, solvent was removed under vacuo and residue was chromatographed using a gradient of AcOEt/Hexane 1:10 to 1:5 as eluent. 6.75 g of an inseparable mixture of cyclopropanated product and $EtO_2CCH=CHCO_2Et$ was obtained. A solution of this mixture in ethanol saturated with hydrogen chloride (250 mL) was stirred overnight at room temperature. The following day, solvent was removed under vacuo and residue taken into ethanol (100 mL). This solution was neutralized with $NaHCO_3$ (solid), filtered and concentrated. The resulting residue was chromatographed using a gradient of AcOEt/

Hexane 1:1 to 3:1 as eluent to give 4.3 g (56% yield) of diol $^1$H-NMR (200 MHz, CDCl$_3$): 1.23 (t, J=7.1 Hz, 3H), 1.49 (t, J=3.5, 1H), 1.89–2.00 (m, 2H), 2.72 (br s, 2H), 3.31–3.42 (m, 2H), 4.05–4.16 (m, 2H) and 4.10 ppm (c, J=7.1 Hz, 2H). $^{13}$C-NMR (50 MHz, CDCl$_3$): 14.0, 23.8, 27.1 (2C), 60.3 (2C), 60.8 and 172.8 ppm.

b) Ethyl (1RS,5SR,6RS)-2-Hydroxy-3-oxabicyclo[3.1.0] hexane-6-carboxylate

To a solution of oxalyl chloride (0.38 mL, 4.48 mmol) in CH$_2$Cl$_2$ (20 mL) at −78° C. under nitrogen atmosphere, dimethylsulfoxide (0.66 mL, 9.33 mmol) was added and stirred for 20 minutes. To this mixture, a solution of the product of step a) (650 mg, 3.73 mL) in CH$_2$Cl$_2$ was added and reaction was stirred at the same temperature for 30 minutes. Then, triethylamine (2.6 mL, 18.65 mmol) was added and mixture allowed to react at room temperature. After 30 minutes, the reaction mixture was quenched with water, the layers were separated and the aqueous layer was extracted with CH$_2$Cl$_2$ (2×). The combined organic layers were dried (Na$_2$SO$_4$), filtered and evaporated to give a residue which was chromatographed using a gradient of AcOEt/Hexane 1:2 to 1:1 as eluent to give 470 mg (73% yield) of lactol. $^1$H-NMR (200 MHz, CDCl$_3$): 1.23 (t, J=7.1 Hz, 3H), 1.43 (t, J=3.3 Hz, 1H), 2.21–2.23 (m, 2H), 2.76 (d, J=3.0 Hz, 1H), 3.85 (d, J=8.7 Hz, 1H), 4.06 (d, J=8.7 Hz, 1H), 4.10 (c, J=7.1 Hz, 2H) and 5.32 (d, J=3.0 Hz, 1H). $^{13}$C-NMR (50 MHz, CDCl$_3$): 14.1, 22.1, 25.0, 31.2, 60.8, 67.3, 97.8 and 171.9 ppm.

c) (2SR) and (2RS)-2-(1'SR,2'RS,3'RS)-2'(ethoxycarbonyl)-3'-hydroxymethylcyclopropyl]glycinonitrile.

A suspension of ammonium chloride (2.42 g, 45.3 mmol) and neutral aluminium oxide (1.4 g) in acetonitrile (50 mL) was ultrasonicated for one hour. A solution of the product of step b) (780 mg, 4.53 mmol) in acetonitrile (20 mL) was then added and ultrasonicated for one hour. After potassium cyanide (3.54 g, 54.36 mmol) finely powdered was added, the mixture was allowed to react for 15 hours. Then, additional aluminium oxide (3.2 g) was added and the reaction mixture was ultrasonicated for 4 days. The mixture was then filtered through celite and the inorganics washed with acetonitrile to give 710 mg (78% yield) of the four possible aminonitriles as a yellow oil.

d) (Alternative 1) Ethyl (2SR,1'SR,2'RS,3'RS)-N-(tert-Butoxycarbonyl)-2-[2'-(ethoxycarbonyl)-3'-hydroxymethylcyclopropyl]glycinate A solution of the product of step c) (380 mg, 1.92 mmol) in ethanol saturated with hydrogen chloride (20 mL) and H$_2$O (0.10 mL, 5.75 mmol) was stirred for one hour at 0° C. and for 48 hours at room temperature. The following day, the solvent was removed in vacuo and the residue was dissolved in ethanol (25 mL). Then, the solution was neutralized with NaHCO$_3$ (solid), filtered through celite and concentrated to dryness. The resulting residue was taken into dioxane (20 mL), and a saturated aqueous solution of NaHCO$_3$ (5 mL) was added. Then, a solution of di-tert-butyldicarbonate (500 mg, 2.3 mmol) in dioxane (5 mL) was added and mixture stirred overnight. The layers were then separated and the aqueous layer was extracted with ethyl acetate (AcOEt). The combined organic layers were dried (Na$_2$SO$_4$), filtered and concentrated to dryness. The residue was purified by column chromatography using AcOEt/Hexane 1:2 as eluent to give 400 mg of a 1:2 mixture of diastereoisomers (61% overall yield). The minor and desired isomer (lower Rf) was separated by column chromatography using AcOEt/Hexane 1:3 as eluent giving rise to ethyl (2SR,1'SR,2'RS,3'RS)-N-(tert-butoxycarbonyl)-2-[2-(ethoxycarbonyl)-3'-hydroxymethylcyclopropyl]glycinate as a mixture of enantiomers.

d) (Alternative 2) Ethyl (2SR,1'SR,2'RS,3'RS)-N-(tert-Butoxycarbonyl)-2-[2-(ethoxycarbonyl)-3'-hydroxymethylcyclopropyl]glycinate A solution of the product of step b) (1.8 g, 10.45 mmol) in EtOH (65 mL) and NaOH (1N) (63 mL, 63.0 mmol) was stirred at 60° C. for 1 hour. The mixture was then cooled to 0° C. and the pH was adjusted to ~6 by addition of 1N KHSO$_4$. To the resulting solution, (NH$_4$)$_2$CO$_3$ (10.1 g, 104.5 mmol) and NaCN (1.02 g, 20.9 mmol) were added. The mixture was stirred under reflux overnight (16–17 hours) and then cooled to room temperature. The solution was then evaporated to dryness under vacuo to give a residue that was taken into MeOH and filtered off. The inorganics were washed with MeOH and the combined methanolic filtrates were concentrated in vacuo. The resulting residue was dissolved in 1N NaOH (200 mL) and the mixture was stirred under reflux for 48 hours and then cooled to 0° C. The pH was then adjusted to 1–2 by addition of 1N HCl, and the solvent was removed under vacuo.

The resulting residue was dissolved in a 1N HCl/ethanol solution (250 mL) and the mixture was stirred overnight at room temperature. The solvent was then removed under vacuo and the residue was taken into EtOH (200 mL). After the solvent was removed under vacuo, the residue was again taken into EtOH (200 mL) and the solution neutralized with NaHCO$_3$ (solid), the inorganics filtered off and the filtrate concentrated to dryness. The residue was taken into dioxane (200 mL) at room temperature and a saturated aqueous solution of NaHCO$_3$ (50 mL) was added. Then, a solution of di-tert-butyldicarbonate (2.75 g, 12.54 mmol) in dioxane (50 mL) was added dropwise and the mixture was vigorously stirred at room temperature overnight. The mixture was then diluted with AcOEt and the layers were separated. The aqueous layer was extracted with AcOEt (2×)and the combined organic layers were dried (Na$_2$SO$_4$), filtered and concentrated to dryness. The residue was purified by column chromatography using AcOEt/hexane (1:2) as eluent to give 2.15 g of a 2.3:1 mixture of diastereoisomers (60% overall yield). The major and desired isomer (lower Rf) was separated by column chromatography using Et$_2$O/Hexane 1:1 as eluent giving rise to ethyl (2SR,1'SR,2'RS,3'RS)-N-(tert-butoxycarbonyl)-2-[2'(ethoxycarbonyl)-3'-hydroxymethylclopropyl]glycinate as a mixture of enantiomers.

$^1$H-NMR (200 MHz, CDCl$_3$): 1.25 (t, J=7.1 Hz, 3H), 1.32 (t, J=7.1 Hz, 3H), 1.45 (s, 9H), 1.70–1.81 (m, 2H), 1.91–2.11 (m, 1H), 3.17 (dd, J=3.1, 10.1 Hz, 1H), 3.54–3.67 (m, 1H),.3.95–4.33 (m, 6H), and 5.20 (br d, J=7.3 Hz, 1H). $^{13}$C-NMR (50 MHz, CDCl$_3$): 14.0, 14.1, 22.5, 28.2 (3C), 28.9, 29.2, 52.3, 60.8, 61.0, 62.5, 80.4, 155.3, 171.8 and 172.4 ppm.

e) Ethyl (2RS,1'SR,2'SR,3'RS)-N-(tert-Butoxycatbonyl)-2-[2'-(ethoxycarbonyl)-3'-vinylcyclopropyl]glycinate.

To a solution of oxalyl chloride (0.38 mL, 4.41 mmol) in CH$_2$Cl$_2$ (30 mL) at −78° C. under nitrogen atmosphere, a solution of dimethylsulfoxide (0.52 mL, 7.35 mmol) in CH$_2$Cl$_2$ (15 mL) was added and stirred for 10 minutes. To this mixture, a solution of a mixture of (2RS) and (2SR) ethyl (1'SR,2'RS,3'RS)-N-(tert-butoxycarbonyl)-2-[2'-(ethoxycarbonyl)-3'-hydroxymethylcyclopropyl]glycinate (1.01 g, 2.94 mmol) (the mixture of products of step d) in CH$_2$Cl$_2$ (5 mL) was added and reaction was stirred at the same temperature for 20 minutes. Then, triethylamine (2.05 mL, 14.7 mmol) was added and mixture allowed to react at room temperature. After 30 minutes, the reaction mixture was quenched with water, the layers were separated and the aqueous layer was extracted with CH$_2$Cl$_2$ (2×). The combined organic layers were dried (Na$_2$SO$_4$), filtered and evaporated to give a residue which was chromatographed using AcOEt/Hexane 1:3 as eluent to give 1.15 g of a mixture of hemiaminals that were used without further purification in the next step.

To a suspension of methyltriphenylphosphonium bromide (2.34 g, 6.55 mmol) in THF (60 mL) at room temperature under nitrogen atmosphere a 0.5M solution of KHMDS in toluene (11.0 mL, 5.5 mmol) was added. After 30 minutes, the mixture was added via cannula to a solution of the mixture of hemiaminals (900 mg, 2.62 mmol) in THF (90 mL) under a nitrogen atmosphere and reaction was stirred for 2 hours. Then, the mixture was poured onto a mixture of Et$_2$O and H$_2$O and the layers were separated. The aqueous layer was extracted with Et$_2$O (2×) and the combined organic layers were dried (Na$_2$SO$_4$), filtered and concentrated to dryness. The residue was purified by column chromatography using AcOEt/hexane (1:2) as eluent giving rise to the ethyl (2RS,1'SR,2'SR,3'RS)-N(tert-butoxycarbonyl)-2-[2'-(ethoxycarbonyl)-3'-vinylcyclopropyl]glycinate as a mixture of enantiomers.

$^1$H-NMR (300 MHz, CDCl$_3$): 1.26 and 1.27 (2 t, J=7.1 Hz, 6H), 1.43 (s, 9H), 1.85–1.77 (m, 1H), 1.99 (t, J=4.9 Hz, 1H), 2.26–2.18 (m, 1H), 3.93–3.87 (m, 1H), 4.32–4.09 (m, 4H), 5.02 (br d, J=7.7 Hz, 1H), 5.20 (d, J=10.4 Hz, 1H), 5.28 (d, J=16.4 Hz, 1H) and 5.70–5.59 ppm (m, 1H). $^1$C-NMR (75 MHz, CDCl$_3$): 14.1 (2C), 26.1, 28.1 (3C), 29.1, 29.2, 52.3, 60.8, 61.3, 80.0, 118.4, 132.4, 154.8, 171.7 and 172.0 ppm.

f) (2RS,1'SR,2'SR,3'RS)-2-(3'-Vinyl-2'carboxycyclopropyl) glycine.

To a solution of the product of step e) (140 mg, 0.41 mmol) in THF (35 mL) was added 2.5N LiOH (6.6 mL, 16.4 mmol). The mixture was vigorously stirred overnight. The organic layer was separated and discarded and the aqueous layer was washed with Et$_2$O. After the aqueous solution was adjusted to pH~1 by addition of 1N HCl at 0° C., it was extracted four times with AcOEt, and the combined organic layers were dried over Na$_2$SO$_4$ and evaporated in vacuo. A solution of the residue in 1N HCl in AcOEt (5 mL) was stirred overnight. The solvent was then removed in vacuo and the resulting solid was washed with Et$_2$O. The hydrochloride was dissolved in MeOH (3 mL) and propylene oxide (10 mL) was added. The mixture was stirred overnight and the resulting insoluble solid was filtered and washed with Et$_2$O to give the title compound (40 mg, 52%).

$^1$H-NMR (200 MHz, D$_2$O): 1.65–1.77 (m, 1H), 1.95 (t, J=5.0 Hz, 1H), 2.06–2.17 (m, 1H), 3.20 (d, J=11.1 Hz, 1H), 5.20–5.05 (m, 2H) and 5.62–5.44 (m, 1H). $^1$C-NMR (50 MHz, D$_2$O): 27.1, 28.8, 29.6, 53.8, 120.5, 132.3, 174.2 and 177.2 ppm.

EXAMPLE 3

(2S,1'S,2'S,3'R)-2-(3'-Methyl-2'-carboxycyclopropyl)glycine a) trans-2-Buten-1-yl Acetoacetate To a refluxing solution of crotyl alcohol (21.5 mL, 252 mmol) and sodium acetate (1.24 g, 15.12mmol) in anhydrous tetrahydrofuran (70 mL) under nitrogen, a solution of diketene (21.34 mL, 277.1 mmol) in anhydrous tetrahydrofuran (30 mL) was. added dropwise over a period of 1 hour. The reaction mixture was heated at reflux for an additional 30 min upon completion of the addition. Then, the reaction mixture was cooled to room temperature and diluted with diethyl ether (300 mL). The resulting solution was washed with a saturated aqueous sodium chloride. solution (2×50 mL) and organic layer. dried over sodium sulfate, filtered and the solvent removed under reduced pressure. The brown residue was purified by column chromatography using a mixture 5:1 of hexane and diethyl ether as eluent to afford 33.0 g (83% yield) of trans-2-buten-1-yl acetoacetate as a colorless liquid.

$^1$H-NMR (200 MHz, CDCl$_3$): 1.72 (dd, J=6.5 and 0.9 Hz, 3H), 2.27 (s, 3H), 3.46 (s, 2H), 4.56 (d, J=6.5 Hz, 2H), 5.65–5.50 (m, 1H), 5.88–5.74 (m, 1H) ppm. $^{13}$C-NMR (50 MHz, CDCl$_3$): 16.9, 29.2, 49.2, 65.0, 124.2, 130.8, 166.3, and 199.7 ppm.

b) trans-2-Buten-1-yl Diazoacetate

To a solution of trans-2-buten-1-yl acetoacetate (40.0 g, 256 mmol) and triethylamine (46.0 mL g, 330 mmol) in anhydrous acetonitrile (250 mL), a solution of p-acetamidobenzenesulfonyl azide (80.0 g, 333 mmol) in anhydrous acetonitrile (250 mL) was added dropwise over a period of 30 minutes. A white precipitate was observed after 15–20 minutes and additional acetonitrile (300 mL) was added to facilitate stirring. The resulting mixture was stirred at room temperature for one additional hour. Then, a solution of lithium hydroxide (35.5 g, 845 mmol) in water (300 mL) was added to the reaction mixture. After stirring for one hour, the resulting mixture was poured onto 2:1 diethylether:ethyl acetate (500 mL) and the layers were separated. The aqueous layer was extracted with 2:1 diethylether:ethyl acetate (500 mL) and the combined organic phases were washed with a saturated aqueous sodium chloride solution (200 mL). The resulting organic solution was dried over sodium sulfate, filtered and the solvent removed under reduced pressure. The residue was purified by column chromatography using a mixture 9:1 of hexane and ethyl acetate as eluent to afford 32.2 g (90% yield) of trans-2-buten-1-yl diazoacetate as a yellow oil.

$^1$H-NMR (200 MHz, CDCl$_3$): 1.72 (dd, J=6.3 and 1.3 Hz, 3H), 4.58 (dt, J=.5.7 and 1.0 Hz, 2H), 5.09 (s, 1H), 5.66–5.50 (m, 1H), 5.89–5.72 (m, 1H) ppm. $^{13}$C-NMR (50 MHz, CDCl$_3$) : 17.1, 45.5, 64.8, 124.8, 130.8, 166.1 ppm.

c) (1S,5R,6R)-(−)-6-Methyl-3-oxabicyclo[3.1.0]hexan-2-one

To a solution of Rh$_2$(5R-MEPY)$_4$ (63.5 mg, 0.082 mmol) in anhydrous dichloromethane (250 mL) heated at reflux, a solution of trans-2-buten-1-yl diazoacetate (5.0 g, 35.7 mmol) in anhydrous dichloromethane (500 mL) was added dropwise over a period of 30 hours. After the addition was complete, the mixture was allowed to react under reflux overnight and then cooled to room temperature. The solvent was removed under reduced pressure and the residue was purified by column chromatography using a gradient mixture of hexane and ethyl acetate from 5:1 to 2:1 as eluent. 3.1 g (77% yield) of (1R,5S,6R)-(−)-6-methyl-3-oxabicyclo [3.1.0]hexan-2-one was obtained as a pale yellow oil with an enantiomeric excess of 64%.* (* Enantiomeric excess was determined by reported methods: J. Am. Chem. Soc. 1995, 117, 5763).

[α]$_D$=−68.5° (c=1.0, CH$_2$Cl$_2$). $^1$H-NMR (200 MHz, CDCl$_3$): 1.16 (d, J=4.8 Hz, 3H), 1.29–1.18 (m, 1H), 1.80–1.84 (m, 1H), 1.96–2.04 (m, 1H), 4.34–4.20 (m, 2H) ppm. $^{13}$C-NMR (50 MHz, CDCl$_3$): 14.9, 19.9, 24.0, 24.2, 68.6, 174.9 ppm.

d) Methyl (1S,2R,3R)-2-Hydroxymethyl-3-methylcyclopropane-1-carboxylate

To a solution of (1R,5S,6R)-(−)-6-methyl-3-oxabicyclo-[3.1.0]hexan-2-one (3.9 g, 34.7 mmol) in tetrahydrofuran (350 mL) at room temperature, a solution of lithium hydroxide (7.29 g, 174 mmol) in water (174 mL) was added. The mixture was stirred overnight at room temperature and the following day the organic phase was removed under vacuo.

The resulting aqueous layer was washed with diethylether (2×50 mL) and then cooled to 0° C. The pH was then adjusted to 2–3 by addition of 1N HCl, and the aqueous layer was extracted with ethyl acetate (6×200 mL). The combined organic phases were dried over sodium sulfate, filtered and the solvent removed under reduced pressure. The resulting (1S,2R,3R)-2-hydroxymethyl-3-methylcyclopropropane-1-carboxylic acid was taken into diethylether (150 mL) and cooled to 0° C. and a solution of diazomethane in diethylether was added in small portions until TLC showed no starting material remained. Solvent was removed under reduced pressure to afford the corresponding methyl (1S,2R,3R)-2-hydroxymethyl-3-methylcyclopropropane-1-carboxylate (5.0. g). This crude was used in the next step without further purification.

$^1$H-NMR (200 MHz, CDCl$_3$): 1.16 (d, J=6.5 Hz, 3H), 1.60–1.38 (m, 3H), 3.69 (s, 3H), 3.78 (dd, J=7.5 and 12.0 Hz, 1H), 3.96 (dd, J=5.5 and 12.0 Hz, 1H) ppm. $^{13}$C-NMR (50 MHz, CDCl$_3$) 16.8, 20.3, 24.7, 31.5, 50.9, 58.8, 172.8 ppm.

d) Methyl (1S,2R,3R)-2-Formyl-3-methylcyclopropropane-1-carboxylate

To a solution of unpurified methyl (1S,2R,3R)-2-hydroxymethyl-3-methylcyclopropropane-1-carboxylate (5.0 g, 34.7 mmol) in anhydrous dichloromethane (350 mL) at room temperature under nitrogen atmosphere, a molecular sieve (4 Å) (3.5 g) was added. After stirring for 15 min, the mixture was cooled to 0° C. and a solution of N-methylmorpholine-N-oxide (6.1 g, 52.1 mmol) was added. After 10 min, tetrapropyl-ammonium perruthenate (490 mg, 1.39 mmol) was added in small portions and the mixture was allowed to react at room temperature. The following day, the solvent was removed under vacuo and the residue was taken into ethyl acetate (200 mL). The resulting suspension was filtered through a plug of celite and organic layer removed to dryness. After purification of the crude by column chromatography using as eluent a gradient of a mixture of ethyl acetate and hexane from 1:6 to 1:4, 3.2 g (66% yield) of methyl (1S,2R,3R)-2-formyl-3-methylcyclopropropane-1-carboxylate were obtained.

[α]$_D$=+22.0° (c=0.75, CH$_2$Cl$_2$). $^1$H-NMR (200 MHz, CDCl$_3$): 1.23 (d, J=6.1 Hz, 3H), 1.89–1.78 (m, 1H), 2.00 (dd, J=6.1 and 8.7 Hz, 1H), 2.27 (sx, J=6.1 Hz, 1H), 3.69 (s, 3H), 9.32 (d, J=6.6 Hz, 1H) ppm. $^{13}$C-NMR (50 MHz, CDCl$_3$): 16.3, 22.3, 30.2, 38.4, 52.0, 170.8, 199.0 ppm.

f) Methyl (1S,2S,3R)-2-Formyl-3-methylcyclopropropane-1-carboxylate

A solution of sodium hydroxide (26.0 g, 650 mmol) in water (260 mL) was added to a solution of methyl (1S,2R,3R)-2-formyl-3-methylcyclopropropane-1-carboxylate (3.2 g, 22.5 mmol) in methanol (315 mL), and the mixture was stirred at room temperature for 3 days. Methanol was then removed under reduced pressure and the resulting aqueous layer was washed with diethylether (2×50 mL) and cooled to 0° C. The pH was then adjusted to 3–4 by addition of an aqueous solution of citric acid (10–25%), and the aqueous layer was extracted with ethyl acetate (6×250 mL). The combined organic phases were dried over sodium sulfate, filtered and the solvent removed under reduced pressure. The resulting carboxylic acid was taken into diethylether (150 mL) and cooled to 0° C., and a solution of diazomethane in diethylether was added in small portions until TLC showed no starting material remained. The solvent was removed under reduced pressure and the residue was purified by column chromatography using hexane and ethyl acetate 4:1 as eluent to afford 2.77 g (83% yield) of an inseparable 5:1 mixture of the corresponding methyl (1S,2S,3R)-2-formyl-3-methylcyclopropropane-1-carboxylate and starting material. This mixture was used in the next step without any other further purification.

$^1$H-NMR (200 MHz, CDCl$_3$): 1.26 (d, J=6.4 Hz, 3H), 2.06–1.97 (m, 1H), 2.31 (dd, J=4.6 and 5.0 Hz, 1H), 2.53 (ddd, J=9.4, 4.6 and 3.6 Hz, 1H), 3.69 (s, 3H), 9.60 (d, J=3.7 Hz, 1H) ppm. $^{13}$C-NMR (50 MHz, CDCl$_3$): 11.0, 24.3, 27.6, 28.7, 52.2, 175.5, 198.0 ppm.

g) (2S,1'S,2'S,3'R,1"R)-N-[(2"-Hydroxy-1"-phenyl)ethyl]2-(2'-methoxycarbonyl-3'-methylcyclopropyl)glycinonitrile To a solution of a 5:1 mixture of methyl (1S,2S,3R)-2-formyl-3-methylcyclopropropane-1-carboxylate and methyl (1S,2R,3R)-2-formyl-3-methylcyclopropropane-1-carboxylate respectively (1.9 g, 13.3 mmol) in methanol (135 mL), (R)-(−)-2-phenylglycinol (2.0 g, 14.7 mmol) was added. The mixture was stirred at room temperature for two hours and then cooled to 0° C. Trimethylsilylcyanide (3.56 mL, 26.7 mL) was added to the mixture and allowed to react at room temperature overnight. The following day the solvent was removed under reduced pressure and the residue was purified by column chromatography using a gradient of a mixture of ethyl acetate and hexane from 1:2 to 1:1 as eluent to afford 4.8 g (88% yield) of a mixture of aminonitriles. (2S,1'S,2'S,3'R,1"R)-N[(2"-hydroxy-1"-phenyl)ethyl] 2-(2"-methoxycarbonyl-3'-methylcyclopropyl) glycinonitrile was found to be the major diastereoisomer in the mixture and was purified and separated by column chromatography using hexane and acetone 7:2 as eluent.

[α]$_D$=−60.5° (c=0.39, CH$_2$Cl$_2$). $^1$H-NMR (200 MHz, CDCl$_3$): 1.09 (d, J=6.4 Hz, 3H), 1.35 (t, J=4.7 Hz, 1H), 1.70–1.56 (m, 1H), 1.88 (dt, J=4.4 and 9.4 Hz, 1H), 2.99 (br d, J=9.1 Hz, 1H), 3.58 (dd, J=9.3 and 10.8 Hz, 1H), 3.70 (s, 3H), 3.79 (dd, J=4.0 and 10.8 Hz, 1H), 4.10 (dd, J=4.0 and 9.3 Hz, 1H), 7.38–7.24 (m, 5H) ppm. $^{13}$C-NMR (50 MHz, CDCl$_3$): 12.5, 21.3, 27.5, 29.3, 46.9, 52.5, 63.3, 67.6, 119.3, 127.9 (2C), 128.8 (2C), 129.4, 138.4, 173.7 ppm.

h) (2S,1'S,2'S,3'R)-3'-Methyl-2'carboxycyclopropyl-glycine

Lead tetraacetate (5.16 g, 11.6 mmol) was added to a solution of (2S,1'S,2'S,3'R,1"R)-N-[(2"-hydroxy-1"-phenyl)ethyl]2-(2'-methoxycarbonyl-3'-methylcyclopropyl) glycinonitrile (2.8 g, 9.7 mmol) in a 1:1 mixture of methanol and dichloromethane (100 mL) at 0° C. After 10 minutes, water (60 mL) was added and the mixture was filtered off through celite. The solvent was removed under reduced pressure and residue taken into 6N HCl (50 mL) and refluxed overnight. The following day, solvent was removed under vacuo to dryness to afford the corresponding hydrochloride salt of (2S,1'S,2'S,3'R)-3'-methyl-2'-carboxycyclopropylglycine. After purification by ion exchange chromatography, 1.5 g (89% yield) of (2S,1'S,2'S, 3'R)-3'-methyl-2'carboxycyclopropylglycine were obtained as a white solid.

EXAMPLE 4

(2S,1'S,2'S,3'R)-2-[3'-(2"-Phenylethyl)-2'carboxycyclopropyl]glycine a) Ethyl (1SR,2SR,3RS) 2-Hydroxymethyl-3-[(2'-Z and E-phenylvinyl)cyclopropanecarboxylate To a suspension of benzyltriphenylphosphonium chloride (11.2 g, 29.03 mmol) in THF (80 ml), KHMDS 0.5 M in toluene (48.76 mL, 24.38 mmol) was added. The resulting suspension was stirred vigorously at room temperature and under argon for 1 hour. Then it was added dropwise via cannula to a solution of ethyl (1RS,5SR,6RS)-2-hydroxy-3-oxabicyclo[3.1.0]-hexane-6-carboxylate (2 g, 11,6 mmol) in THF (30 mL). The mixture was stirred 1 hour at room temperature, and then poured onto a mixture of ether-H$_2$O 1:1. The organic layer was dried (MgSO$_4$), filtrated and evaporated in vacuo. The residue was purified by column chromatography using AcOEt/hexane (1:2) as eluent to give 2.2 g (78% yield) of an inseparable mixture of ethyl (1SR, 2SR,3RS) 2-hydroxymethyl-3-[(2'-Z and E-phenylvinyl) cyclopropanecarboxylate as a yellow oil that was used in the next step without further purification.

b) Ethyl (1SR,2SR,3RS) 2-Hydroxymethyl-3-(2'-phenylethyl)cyclopropanecarboxylate.

To a solution of ethyl (1SR,2SR,3RS) 2-hydroxymethyl-3-[(2'-Z, and E-phenylvinyl)cyclopropanecarboxylate (1.6 g, 6.8 mmol) in MeOH (50 mL), Pd (C) 5% (0.32 g, 20% of the olefin weight) was added. The mixture was hydrogenated with a balloon filled with hydrogen at room temperature overnight. Then, the mixture was filtrated through celite and the solvent evaporated in vacuo to give 1.39 g (83% yield) of ethyl (1SR,2SR,3RS) 2-hydroxymethyl-3-(2'-phenylethyl)cyclopropanecarboxylate as colorless oil. The oil was used without purification.

$^1$H-NMR (300 MHz, CDCl$_3$): 1.24 (t, J=7.1 Hz, 3H), 1.53–1.60 (m, 1H), 1.69–1.81 (m, 4H), 2.74 (t, J=7.7 Hz, 2H), 3.47–3.54 (m, 1H), 3.58–3.65 (m, 1H), 4.09 (q, J=7.1 Hz, 2H) and 7.15–7.31 (m, 5H). $^{13}$C-NMR (75 MHz, CDCl$_3$): 14.1, 24.9, 2.6.6, 27.8, 29.2, 35.7, 60.5, 60.6, 125.9, 128.3, 128.4, 141.4, and 173.6 ppm.

c) Ethyl (1SR,2SR,3RS) 2-Formyl-3-(2'-phenylethyl) cyclopropanecarboxylate.

To a solution of ethyl (1SR,2SR,3RS) 2-hydroxymethyl-3-(2'-phenylethyl)cyclopropanecarboxylate (1.15 g, 4.6 mmol) in CH$_2$Cl$_2$ (40 mL) at room temperature and under argon, a molecular sieve (4 Å) (2.2 g) was added. After stirring 5 minutes, NMO (0.54 g, 4.6 mmol) and TPAP (0.03 g, 0.09 mmol) were added and the mixture was stirred overnight. Then the reaction mixture was filtered through celite and the solvent was removed to dryness. After purification of the crude by column chromatography using AcOEt/Hexane 1:6 as eluent, 0.7 g (63% yield) of ethyl (1SR,2SR,3RS) 2-formyl-3-(2'-phenylethyl) cyclopropanecarboxylate was obtained as yellow oil.

$^1$H-NMR (300 MHz, CDCl$_3$): 1.25 (t, J=7.1 Hz, 3H), 1.73–1.82 (m, 1H), 1.93–1.98 (m, 2H), 2.27 (t, J=5.5 Hz, 1H), 2.45–2.51 (m, 1H), 2.58–2.74 (m, 2H), 4.11 (q, J=7.1 Hz, 2H), 7.12–7.29 (m, 5H) and 9.38 (d, J=3.3 Hz, 1H). $^{13}$C-NMR (75 MHz, CDCl$_3$): 14.1, 27.7, 27.7, 31.2, 35.3, 35.5, 61.0, 126.0, 128.3, 128.4, 140.4, 171.2 and 197.4 ppm.

d) (2S,1'S,2'S,3'R,1"R)-N-[(2"-Hydroxy-1"-phenyl)ethyl]-2-[2'-(ethoxycarbonyl)-3'-(2-phenylethyl)cyclopropyl] glycinonitrile To a solution of ethyl (1SR,2SR,3RS)-2-formyl-3(2'-phenylethyl)cyclopropanecarboxylate (0.78 g, 3.2 mmol) in MeOH (50 mL), (R)-α-phenylglycinol (0.48 g, 3.5 mmol) was added. The resulting solution was stirred at room temperature for 2 hours. After cooling to 0° C., TMSCN (0.63 g, 6.4 mmol) was added, and the resulting mixture was stirred for 12 hours at room temperature. Evaporation of the solvent gave 1.2 g (96%) of a mixture of two diastereoisomers. The mixture was separated by column chromatography using Acetone/Hexane 2:7 as eluent to afford 0.28 g of pure isomer A, and 0.22 g of pure isomer B.

Isomer A: (2S,1'S,2'S,3'R,1"R)-N-(2"-Hydroxy-1"-phenyl) ethyl-2-[2'-(ethoxycarbonyl)-3'-(2-phenylethyl) cyclopropyl]glycinonitrile.

$^1$H-NMR (300 MHz, CDCl$_3$): 1.20 (t, J=7.1 Hz, 3H), 1.26 (t, J=4.9 Hz, 1H), 1.30–1.39 (m, 1H), 1.44–1.54 (m, 1H), 1.66–1.77 (m, 1H), 1.84 (t-d, J$_1$=9.4 Hz, J$_2$=4.4 Hz, 1H), 2.37 (1-broad, 1H), 2.59–2.65 (m, 2H) , 2.92 (d, J=9.4 Hz, 1H), 1H), 3.48 (t, J=10.4 Hz, 1H) 3.67 (d-d, J$_1$=0.4 Hz, J$_2$=3.9 Hz, 1H), 3.98–4.09 (m, 3H) and 6.99 (d, J=6.6 Hz, 2H) , 7.08–7.27 (m, 8H). $^{13}$C-NMR (75 MHz, CDCl$_3$): 14.1, 26.1, 26.2, 28.6, 29.2, 35.4, 46.4, 60.9, 62.8, 67.1, 118.9, 126.0, 127.4, 128.2, 128.3, 128.3, 128.9, 137.8, 140.7, and 172.5 ppm.

Isomer B: (2S,1'R,2'R,3'S,1"R)-N-[(2"-Hydroxy-1"-phenyl) ethyl]-2-[2'-(ethoxycarbonyl)-3-(2-phenylethyl) cyclopropyl]glycinonitrile $^1$H-NMR (300 MHz, CDCl$_3$): 1.24 (t, J=7.1 Hz, 3H) 1.26–1.32 (m, 2H) 1.54–1.64 (m, 1H), 174–1.84 (m, 1H), 1.91 (t-d, J$_1$=9.4 Hz, J$_2$=4.4 Hz, 1H), 2.48 (s-broad, 1H), 2.65–2.82 (m, 2H), 2.88 (d, J=9.9 Hz, 1H), 3.61 (t, J=10.9 Hz, 1H), 3.77 (d-t, J$_1$=10.9 Hz, J$_2$=3.9 Hz, 1H), 4.06 (t, J=4.9 Hz, 1H), 4.10 (q, J=7.1 Hz, 2H) and 7.09 (d, J=6.6 Hz, 2H) 7.23–7.34 (m, 8H). $^{13}$C-NMR (75 MHz, CDCl$_3$): 14.1, 25.0, 27.0, 28.5, 28.6, 35.2, 47.1, 60.9, 63.1, 67.0, 118.9, 126.0, 127.8, 128.2, 128.3, 128.4, 128.8, 137.6, 140.9 and 172.3 ppm e) (2S,1'S,2'S,3'R)-2-[3'-(2"-Phenylethyl)-2'-carboxycyclopropyl]-glycine Lead(IV)acetate (0.34 g, 0.76 mmol) was added to a cold (0° C.) stirred solution of (2S,1'S,2'S,3'R,1"R)-N-[(2"-hydroxy-1"-phenyl)ethyl]-2-[2'-(ethoxycarbonyl)-3'-(2-phenylethyl)cyclopropyl]glycinonitrile, (0.28 g, 0.69 mmol) in 6 mL of an anhydrous 1:1 CH$_2$Cl$_2$-MeOH mixture (0,12 M) and stirred for 10 minutes. Water was added 6 mL) and the resulting mixture filtered through celite. After evaporation of the solvent, the residue was refluxed in 6 N HCl (16 mL) for 18 hours. The reaction mixture was washed with CH$_2$Cl$_2$ and evaporated to dryness. The resulting residue was purified by ion exchange chromatography to afford (2S,1'S,2'S,3'R)-2-[3'-(2"-phenylethyl)-2'-carboxycyclopropyl]-glycine as a white solid.

$^{13}$C-NMR (50 MHz, D$_2$O): 25.5, 26.1, 27.7, 28.8, 34.0, 54.1, 124.7, 127.3 (2C), 127.5 (2C), 141.1, 172.4, 179.6 ppm.

EXAMPLE 5

(2SR,1'SR,2'SR,3'RS)-2-[3'-Vinyl-2'-carboxycyclopropyl]glycine

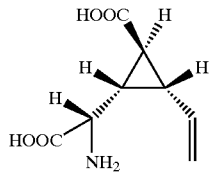

a) Ethyl (1SR,2SR,3RS)-2-Hydroxymethyl-3-vinylcyclopropane Carboxylate.

To a suspension of methyltriphenylphosphonium bromide (5.2 g, 14.5 mmol) in anhydrous dioxane (75 mL) at room temperature under a nitrogen atmosphere, a 0.5M solution of potassium bis(trimethylsilyl)amide in toluene (24.4 mL, 12.2 mmol) was added. After 1 hour, the mixture was added via cannula to a solution ethyl (1RS,5SR,6RS)-2-hydroxy-3-oxabicyclo[3.1.0]-hexane-6-carboxylate (1.0 g, 2.62 mmol) in anhydrous dioxane (25 mL) under a nitrogen atmosphere and the reaction mixture was stirred for 1 hour. Then, the mixture was poured onto a 2:1 mixture of diethyl ether and water (300 mL) and the layers were separated. The aqueous layer was extracted with diethyl ether (2×100 mL) and the combined organic layers were dried over sodium sulfate, filtered and concentrated to dryness. The residue was purified by column chromatography using ethyl acetate and hexane 1:2 as eluent to afford 840 mg (85% yield) of ethyl (1SR,2SR,3RS)-2-hydroxymethyl-3-vinylcyclopropane carboxylate.

¹H-NMR (200 MHz, CDCl₃): 1.25 (t, J=7.1 Hz, 3H), 1.71 (t, J=4.7 Hz, 1H), 1.88–2.02 (m, 1H), 2.16–2.29 (m, 1H), 3.53–3.65 (m, 1H), 3.71–3.83 (m, 1H), 4.11 (c, J=7.1 Hz, 2H), 5.11–5.32 (m, 2H), 5.52–5.69 ppm (m, 1H).

b) Ethyl (1SR,2SR,3RS)-2-Formyl-3-vinylcyclopropane Carboxylate.

To a solution of oxalyl chloride (0.30 mL, 3.5 mmol) in anhydrous dichloromethane (30 mL) at −78° C. under nitrogen atmosphere, dimethylsulfoxide (0.51 mL, 7.2 mmol) was added and stirred for 30 minutes. To this mixture, a solution of ethyl (1SR,2SR,3RS)-2-hydroxymethyl-3-vinylcyclopropane carboxylate (490 mg, 2.9 mmol) in anhydrous dichloromethane (20 mL) was added and reaction stirred at the same temperature for 45 minutes. Then, triethylamine (2.0 mL, 14.4 mmol) was added and mixture was allowed to react at room temperature. After 30 minutes, the reaction was quenched with water (30 mL), the layers were separated and the aqueous one was extracted with dichloromethane (2×30 mL). The combined organic layers were dried over sodium sulfate, filtered and evaporated. The resulting residue was purified by column chromatography using ethyl acetate and hexane 1:4 as eluent to afford 460 mg (95% yield) of ethyl (1SR,2SR,3RS)-2-formyl-3-vinylcyclopropane carboxylate.

¹H-NMR (200 MHz, CDCl₃): 1.26 (t, J=7.1 Hz, 3H), 2.61–2.77 (m, 3H), 4.16 (c, J=7.1 Hz, 2H), 5.13–5.37 (m, 2H), 5.63–5.82 (m, 1H) and 9.56 ppm (d, J=4.0 Hz, 1H).

c) (2SR,1'SR,2'SR,3'RS)-N-Acetyl-2-[2'-(ethoxycarbonyl)-3'-vinylcyclopropyl]glycinonitrile.

A suspension of ammonium chloride (1–94 g, 36.3 mmol) and neutral aluminium oxide (3.65 g) in anhydrous acetonitrile (18 mL) was ultrasonicated for one hour. A solution of ethyl (1SR,2SR,3RS)-2-formyl-3-vinylcyclopropane carboxylate (615 mg, 3.66 mmol) in anhydrous acetonitrile (18 mL) was added and ultrasonicated for one hour. Potassium cyanide (2.8 g, 44.0 mmol) finely powdered was then added, and the mixture was allowed to react for 17 hours. The mixture was filtered through celite and the solvent was evaporated. The resulting residue was purified by column chromatography using ethyl acetate and hexane 3:1 to give 780 mg (90% yield) of a racemic mixture of (2SR) and (2RS)-(1'SR,2'SR,3'RS)-2-[2'-(ethoxycarbonyl)-3'-vinylcyclopropyl]glycinonitrile. Both isomers were separated by column chromatography using ethyl acetate and hexane 3:2.

To a solution of (2SR,1'SR,2'SR,3'RS)-2-[2'-(ethoxycarbonyl)-3'-vinylcyclopropyl]glycinonitrile (190 mg, 0.96 mmol) in anhydrous dichloromethane (10 mL) at 0° C. under nitrogen atmosphere, N,N-diisopropylethylamine (0.21 mL, 1.20 mmol) was added and stirred for 15 minutes. Then, acetyl chloride (0.08 mL, 1.10 mmol) was added, and the reaction mixture was stirred a room temperature. After 3 hours, the reaction was quenched with water (5 mL), the layers were separated and the aqueous one was extracted with dichloromethane (2×10 mL). The combined organic layers were dried over sodium sulfate, filtered and evaporated to give a residue which was purified by column chromatography using ethyl acetate and hexane 1.5:1 as eluent to give 225 mg (90% yield) of (2SR,1'SR,2'SR,3'RS)-N-acetyl-2-[2'(ethoxycarbonyl)-3-vinylcyclopropyl]glycinonitrile.

¹H-NMR (200 MHz, CDCl₃): 1.24 (t, J=7.1 Hz, 3H), 1.92–2.21 (m, 3H), 2.01 (s, 3H), 2.25–2.34 (m, 1H), 4.11 (dc, J=1.8 and 7.1 Hz, 2H), 4.59 (dd, J=8.2 and 10.3, 2H), 5.27–5.40 (m, 2H), 5.72 (ddd, J=7.4, 10.3 and 17.0, 1H), 6.94 (d, J=8.2 Hz, 1H). ¹³C-NMR (50 MHz, CDCl₃): 171.5, 169.6, 130.5, 120.5, 117.3, 61.3, 39.2, 29.2, 28.6, 25.7, 22.7, 14.0.

d) (2SR,1'SR,2'SR,3'RS)-2-(3'-Vinyl-2'carboxycyclopropyl)glycine.

A solution of (2SR,1'SR,2'SR,3'RS)-N-acetyl-2-[2'-(ethoxycarbonyl)-3'-vinylcyclopropyl]glycinonitrile (200 mg, 0.84 mmol) in 1N HCl (6 mL) was refluxed for 21 hours and then the solvent was removed in vacuo. The residue was purified by ion exchange chromatography to afford 90 mg (60% yield) of (2SR,1'SR,2'SR,3'RS)-2-(3'-vinyl-2'-carboxy cyclopropyl)glycine.

¹³C-NMR (50 MHz, D₂O): 175.5, 173.4, 133.0, 119.7, 54.6, 31.6, 28.9, 25.7.

EXAMPLE 6

(2SR,1'SR,2'SR,3'RS)-2-[3'-Ethyl-21 carboxycyclopropyl]glycine

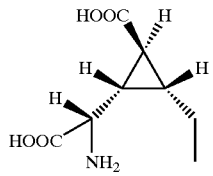

a) Ethyl (1SR,2SR,3RS)-3-Ethyl-2-hydroxymethyl Cyclopropane Carboxylate.

A suspension of a mixture of ethyl (1SR,2SR,3RS)-2-hydroxymethyl-3-vinylcyclopropane carboxylate (500 mg, 2.94 mmol) and 5% palladium on carbon (70-mg) in methanol (25 mL) was stirred under hydrogen atmosphere overnight. The catalyst was then filtered off through celite and the solvent was removed under vacuo. The residue was purified by column chromatography using ethyl acetate and hexane 1:2 as eluent to give 380 mg (80% yield) of ethyl (1SR,2SR,3RS)-3-ethyl-2-hydroxymethylcyclopropane carboxylate.

¹H-NMR (300 MHz, CDCl₃): 1.07 (t, J=7.1 Hz, 3H), 1.30 (t, J=7.1 Hz, 3H), 1.35 (t, J=4.4 Hz, 1H), 1.43–1.59 (m, 3H), 1.80–1.89 (m, 2H), 3.71 (d, J=7.1 Hz, 2H) and 4.15 ppm (c, J=7.1 Hz, 2H). ¹³C-NMR (75 MHz, CDCl₃): 13.9, 14.2, 20.7, 25.1, 28.8, 29.1, 60.5, 60.9 and 173.8 ppm.

d) Ethyl (1SR,2SR,3RS)-2-Formyl-3-ethylcyclopropane Carboxylate.

To a solution of oxalyl chloride (0.21 mL, 2.4 mmol) in anhydrous dichloromethane (30 mL) at −78° C. under nitrogen atmosphere, dimethylsulfoxide (0.36 mL, 5.0 mmol) was added and stirred for 30 minutes. To this mixture, a solution of ethyl (1SR,2SR,3RS)-2-hydroxymethyl-3-ethylcyclopropane carboxylate (350 mg, 2.0 mmol) in anhydrous dichloromethane (20 mL) was added and reaction stirred at the same temperature for 45 minutes. Then, triethylamine (1.4 mL, 10.0 mmol) was added and the mixture was allowed to react at room temperature. After 30 minutes, the reaction was quenched with water (30 mL), the layers were separated and the aqueous one was extracted with dichloromethane (2×50 mL). The combined organic layers were dried over sodium anhydride, filtered and evaporated to dryness. The resulting residue was purified by column chromatography using ethyl acetate and hexane 1:4 as eluent to afford 310 mg (90% yield) of ethyl (1SR,2SR,3RS)-2-formyl-3-ethylcyclopropane carboxylate.

¹H-NMR (300 MHz, CDCl₃): 0.98 (t, J=7.7 Hz, 3H), 1.27 (t, J=7.1 Hz, 3H), 1.43–1.58 (m, 1H), 1.62–1.74 (m, 1H), 1.92–2.02 (m, 1H), 2.33–2.37 (m, 1H), 2.49–2.55 (m, 1H), 4.15 (c, J=7.1 Hz, 2H) and 9.59 ppm (d, J=3.8 Hz, 1H). ¹C-NMR (75 MHz, CDCl₃): 13.7, 14.0, 19.7, 28.0, 33.4, 35.6, 61.0, 171.2 and 197.7 ppm.

c) (2SR,1'SR,2'SR,3'RS)-N-Acetyl-2-[2'(ethoxycarbonyl)-3'-ethylcyclopropyl]glycinonitrile.

A suspension of ammonium chloride (5.53 g, 103.5 mmol) and neutral aluminium oxide (10.35 g) in anhydrous acetonitrile (70 mL). was ultrasonicated for one hour. A solution of ethyl (1SR,2SR,3RS)-2-formyl-3-ethylcyclopropane carboxylate (1.76 g, 10.3 mmol) in anhydrous acetonitrile (70 mL) was added and ultrasonicated for one hour. Potassium cyanide (8.10 g, 124.3 mmol) finely powdered was then added, and the mixture was allowed to react for 2 days. The mixture was filtered through celite and the solvent was evaporated. The resulting residue (1.92 g) was taken into anhydrous dichloromethane (100 mL) and mixture cooled to 0° C. Then, N,N-diisopropylethylamine (2.23 mL, 12.7 mmol) was added to the mixture under nitrogen atmosphere, and stirred for 15 minutes. Then, acetyl chloride (0.84 mL, 11.8 mmol) was added, and the reaction mixture was stirred a room temperature. After 3 hours, the reaction was quenched with water (40 mL), the layers were separated and the aqueous one was extracted with dichloromethane (2×100 mL). The combined organic layers were dried over sodium sulfate, filtered and evaporated. The residue was purified by column chromatography using hexane and ethyl acetate 1:1 as eluent to give 1.73 g (70% yield) of a 1:1 mixture of the corresponding racemic acetylated aminonitriles. Both isomers were separated by recrystallization. Isomer A was precipitated by recrystallization in diethyl ether while isomer B remained in the solvent.

Isomer A: (2RS,1'SR,2'SR,3'RS)-N-Acetyl-2-[2'(ethoxycarbonyl)-3'-ethylcyclopropyl]glycinonitrile $^1$H-NMR (300 MHz, CDCl$_3$): 1.00 (t, J=7.1 Hz, 3H), 1.29(t, J=7.1 Hz, 3H), 1.37–1.59 (m, 4H), 1.91–1.99 (m, 1H), 2.06 (s, 3H), 4.15 (q, J =7.1 Hz, 2H), 4.62 (dd, J=10.4 Hz, J$_2$=8.3 Hz, 1H), 6.08 (dd, J$_1$=8.3 Hz, J$_2$=1.1 Hz, 1H). $^{13}$C-NMR (75 MHz, CDCl$_3$): 13.6, 14.0, 20.3, 22.5, 25.1, 28.4, 29.6, 39.0, 61.3, 118.1, 169.3, 172.7 ppm Isomer B: (2SR,1'SR,2'SR,3'RS)-N-Acetyl-2-[2'(ethoxycarbonyl)-3'-ethylcyclopropyl]glycinonitrile $^1$H-NMR (300 MHz, CDCl$_3$): 1.12 (t, J=7.1 Hz, 3H), 1.27 (t, J =7.1 Hz, 3H) , 1.45–1.72 (m, 4H), 1.92–2.00 (m, 1H), 2.07 (s, 3H), 4.07–4.18 (m, 2H), 4.60 (dd, J$_1$=10.4 Hz, J$_2$=8.3 Hz, 1H), 6.05 (d, J$_1$=7.6 Hz, 1H). $^{13}$C-NMR (75 MHz, CDCl$_3$): 13.8, 14.1, 20.9, 22.8, 25.8, 28.6, 29.0, 38.9, 61.1, 117.7, 169.4, 172.5 ppm d) (2SR,1'SR,2'SR,3'RS)-2-[3'-Ethyl-2'carboxycyclopropyl] glycine A solution of (2SR,1'SR,2'SR,3'RS)-N-acetyl-2-[2'-(ethoxycarbonyl)-3'-ethylcyclopropyl]glycinonitrile (300 mg, 1.3 mmol) in 6N HCl (13 mL) was refluxed overnight. The solvent was removed in vacuo, and residue was washed with diethyl ether and then taken into methanol (4 mL). To this solution, propylene oxide (9 mL) was added and mixture was stirred overnight. The resulting white solid was filtered, washed with diethyl ether and dried under vacuo to give 160 mg (65% yield) of (2SR,1SR,2'SR,3'RS)-2-(3'-ethyl-2-'carboxycyclopropyl)glycine.

$^1$H-NMR (300 MHz, D$_2$O): 0.83 (t, J=7.1 Hz, 3H), 1.01–1.03 (m, 1H), 1.13–1.14 (m, 1H), 1.28–1.31 (m, 1H), 1.41–1.44 (m, 1H), 1.55–1.59 (m, 1H), 3.20 (d, J=11.0 Hz, 1H) $^{13}$C-NMR (75 MHz, D$_2$O) 15.6, 23.8, 29.9, 30.5, 31.9, 57.3, 176.4, 183.9 ppm.

EXAMPLE 7

(2SR,1'SR,2'SR,3,RS)-2-[3'-Propyl-2'-carboxycyclopropyl]glycine

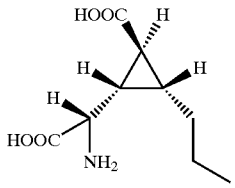

a) Ethyl (1SR,2SR,3RS)-2-Hydroxymethyl-3-(1-propenyl) cyclopropane Carboxylate.

To a suspension of ethyltriphenylphosphonium bromide (5.38 g, 14.5 mmol) in anhydrous dioxane (75 mL) at room temperature under a nitrogen atmosphere a 0.5M solution of KHMDS in toluene (24.4 mL, 12.2 mmol) was added. After 1 hour, the mixture was added via cannula to a solution of ethyl (1RS,5SR,6RS)-2-hydroxy-3-oxabicyclo[3.1.0]-hexane-6-carboxylate (1 g, 5.81 mmol) in dioxane (25 mL) under a nitrogen atmosphere and the reaction mixture was stirred for 1 hour. Then, the mixture was poured onto a mixture of Et$_2$O and H$_2$O and the layers were separated. The aqueous layer was extracted with Et$_2$O (2×) and the combined organic layers were dried (Na$_2$SO$_4$), filtered and concentrated to dryness. The residue was purified by column chromatography using AcOEt/hexane (1:2) as eluent to give 748 mg (70% yield) of the ethyl (1SR,2SR,3RS)-2-hydroxymethyl-3-(1'-propenyl)cyclopropane-carboxylate as a mixture of enantiomers.

$^1$H-NMR (200 MHz, CDCl$_3$): 1.25 (t, 3H), 1.5–1.7 (m, 4H), 1.9–2.0 (m, 1H), 2.3 (m, 1H), 3.6 (t,1H), 3.7 (s,1H), 4.1 (m, 2H), 5.1 (m, 1H), 5.7 (m, 1H). $^{13}$C-NMR (50 MHz, CDCl$_3$): 13.3,14.1, 18.0, 24.3, 25.8, 27.0, 28.7, 29.3, 29.4, 32.4, 60.7, 61.0, 61.2, 125.1, 125.4, 128.4, 129.0, 173.0.

b) Ethyl (1SR,2SR,3RS)-3-Propyl-2-hydroxymethyl Cyclopanecarboxylate

A suspension of a mixture of ethyl (1SR,2SR,3RS)-2-hydroxymethyl-3-(1'-propenyl)cyclopropane carboxylate (680 mg, 3.69 mmol) and 10% palladium on carbon (88 mg) in MeOH (31 mL) was stirred under hydrogen atmosphere overnight. The catalyst was then filtered off through celite and the solvent was removed under vacuo. The residue was chromatographed using AcOEt/Hexane 1:2 as eluent to give 446 mg (65% yield) of the corresponding alcohol.

$^1$H-NMR (200 MHz, CDCl$_3$): 0.89 (t, 3H), 1.18–1.49 (m, 11H), 3.64 (m, 2H), 4.06 (c, 2H). $^{13}$C-NMR (50 MHz, CDCl$_3$): 13.7, 14.1, 22.7, 25.3, 26.9, 28.8, 29.3, 60.5, 60.8, 173.9.

c) Ethyl (1SR,2SR,3RS)-2-Formyl-3-propylcyclopropane Carboxylate.

To a solution of oxalyl chloride (0.5 mL, 5.76 mmol) in CH$_2$Cl$_2$ (71 mL) at -78° C. under a nitrogen atmosphere, dimethylsulfoxide (0.85 mL, 12.0 mmol) was added and stirred for 30 minutes. To this mixture, a solution of ethyl (1SR,2SR,3RS)-2-hydroxymethyl-3-propylcyclopropanecarboxylate (783 mg, 4.2 mmol) in CH$_2$Cl$_2$ (10 mL) was added and the reaction mixture was stirred at the same temperature for 45 minutes. Then, triethylamine (3.33 mL, 24 mmol) was added and mixture was allowed to react at room temperature. After 30 minutes, the reaction was quenched with water, the layers were separated and the aqueous one was extracted with CH$_2$Cl$_2$ (2×). The combined organic layers were dried (Na$_2$SO$_4$), filtered and evaporated to give a residue which was chromatographed using AcOEt/Hexane 3:7 as eluent to give 697 mg (90% yield) of aldehyde.

¹H-NMR (200 MHz, CDCl₃): 0.93 (t,3H), 1.21–1.6 (m,7H), 1.97 (m, 1H), 2.32 (t, 1H), 2.48 (m, 1H), 4.12 (c,2H), 9.55 (d, 1H). ¹³C-NMR (50 MHz, CDCl₃): 13.5, 14.2, 22.7, 28.1, 28.3, 31.7, 35.6, 61.1, 171.4, 198.0.

d) (2SR) and (2RS)-N-Acetyl-(1'SR,2'SR,3'RS)-2-(2'(ethoxycarbonyl)-3-'-propylcyclopropyl)glycinonitrile A suspension of ammonium chloride (1.99 g, 37.2 mmol) and neutral aluminium oxide (3.74 g) in acetonitrile (18 mL) was ultrasonicated for one hour. A solution of ethyl (1SR, 2SR,3RS)-2-formyl-3-propylcyclopropane carboxylate (687 mg, 3.73 mmol) in acetonitrile (18 mL). was added and ultrasonicated for one hour. Potassium cyanide (2.87 g, 44.0 mmol) finely powdered was then added, and the mixture was allowed to react for 17 hours. The mixture was filtered through celite and the solvent was evaporated to give aminonitrile as a mixture of diasteroisomers.

To a solution of the mixture of aminonitriles (757 mg, 3.6 mmol) in CH₂Cl₂ (33 mL) at 0° C. under nitrogen atmosphere, N,N-diisopropylethylamine (0.75 mL) was added and stirred for 15 minutes. Then, acetyl chloride (0.31 mL) was added, and the reaction mixture was stirred a room temperature. After 3 hours, the reaction was quenched with water, the layers were separated and the aqueous one was extracted with CH₂Cl₂ (2×). The combined organic layers were dried (Na₂SO₄), filtered and evaporated to give a residue which was purified by flash chromatography using hexane and ethyl acetate 1:2 to afford 826 mg (88% yield) of a 1:1 racemic mixture of the corresponding acetylated glycinonitriles nitriles. Both diastereoisomers were separated by column chromatography using. hexane and ethyl acetate 1:1.5.

Diastereoisomer 1: (2RS,1'SR,2'SR,3'RS)-N-Acetyl-2-(2'-(ethoxycarbonyl)-3'-propylcyclopropyl)glycinonitrile ¹H-NMR (200 MHz, CDCl₃): 0.8 (t, 3H), 1.2–1.6 (m, 9H), 1.8–2.0 (m, 1H), 2.1 (s,3H), 4.1 (c, 2H), 4.5.(dd, 1H), 6.8 (d, 1H). ¹³C-NMR (50 MHz, CDCl₃): 13.6, 14.1, 22.5, 22.6, 27.7, 28.1, 28.2, 28.7, 39.1, 61.3, 118.1, 169.1, 172.6.

Diastereoisomer 2: (2SR,1'SR,2'SR,3'RS)-N-Acetyl-2-(2'-(ethoxycarbonyl)-3'-propylcyclopropyl)glycinonitrile ¹H-NMR (200 MHz, CDCl₃): 0.9 (t, 3H), 1.2–1.6 (m, 9H), 1.8–2.0 (m, 1H), 2.1 (s, 3H), 4.1 (c, 2H), 4.5 (dd, 1H), 6.5 (d, 1H). ¹³C-NMR (50 MHz, CDCl₃): 13.6, 14.1, 22.6, 22.7, 26.0, 27.1, 28.2, 29.3, 39.1, 61.1, 117.7, 169.4, 172.5.

e) (2SR,1'SR,2'SR,3'RS)-2-(3'-Propyl-2'-carboxy Cyclopropyl)glycine.

A solution of (2SR,1'SR,2'SR,3'RS)-N-acetyl-(2-(2'-(ethoxycarbonyl)-3'-propylcyclopropyl)glycinonitrile (249 mg, 1.0 mmol) in 6N HCl (10 mL) was refluxed for 16 hours. The solvent was then removed in vacuo and the resulting solid was washed with diethyl ether. The hydrochloride was dissolved in methanol (3 mL) and propylene oxide (10 mL) was added. The mixture was stirred overnight and the resulting insoluble solid was filtered and washed with diethyl ether to give 185 mg (93% yield) of the title compound.

¹³C-NMR (50 MHz, D₂O): 14.3, 23.5, 27.8, 30.0, 30.8, 32.5, 57.1, 182.9, 184.2.

What is claimed is:

1. A compound of the formula:

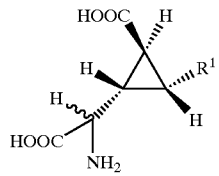

in which $R^1$ is $C_{1\text{-}10}$ alkyl; $C_{2\text{-}10}$ alkenyl; $C_{2\text{-}10}$ alkynyl; phenyl-$C_{2\text{-}10}$ alkyl or phenyl-$C_{2\text{-}10}$ alkenyl; or a salt or ester thereof.

2. A compound as claimed in claim 1, which has the configuration

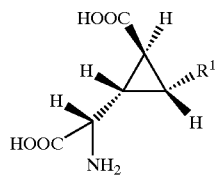

3. A compound as claimed in claim 1 or claim 2, in which $R^1$ is $C_{1\text{-}10}$ alkyl; $C_{2\text{-}10}$ alkenyl or $C_{2\text{-}10}$ alkynyl.

4. A compound as claimed in claim 1 or claim 2, in which $R^1$ is selected from methyl, ethyl, propyl, isopropyl, vinyl, prop-2-enyl and propynyl.

5. A compound as claimed in claim 1 or claim 2, in which $R^1$ is methyl or vinyl.

6. A compound as claimed in claim 1 which is selected from:

(2S,1'S,2'S,3'R)-2-(3'-methyl-2'-carboxycyclopropyl)-glycine;

(2S,1'S,2'S,3'R)-2-[3'-(2"-ethyl)-2'-carboxycyclopropyl] glycine;

(2S,1'S,2'S,3'R)-2-[3'-(3"-propyl)-2'-carboxycyclopropyl] glycine;

(2SR,1'SR,2'SR,3'RS)-2-(3'-vinyl-2'carboxycyclopropyl)-glycine; and (2S,1'S,2'S,3'R)-2-[3'-(2"-phenylethyl)-2'carboxycyclopropyl]glycine;

and pharmaceutically acceptable salts and esters thereof.

7. A pharmaceutical formulation comprising a compound of formula I as claimed in any one of claims 1, 2 or 6, or a pharmaceutically acceptable metabolically labile ester thereof, or a pharmaceutically acceptable salt thereof, together with a pharmaceutically acceptable carrier, diluent or excipient.

8. A process for preparing a compound of formula I as claimed in any one of claims 1, 2 or 6, or a salt or ester thereof, which comprises:

(a) deprotecting a compound of formula

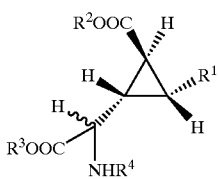

II in which $R^1$ represents any of the values defined in claim 1, $R^2$ and $R^3$ each independently represents hydrogen or a carboxyl protecting group, and $R^4$ represents hydrogen or an amine protecting group;

(c) hydrolysing a compound of formula

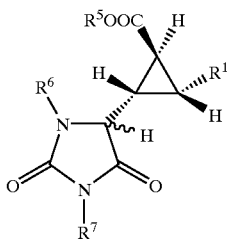

III in which $R^1$ represents any of the values defined in claim 1, $R^5$ represents a hydrogen atom or a carboxyl protecting group, $R^6$ is a hydrogen atom and $R^7$ represents a hydrogen atom, a $C_{1-4}$ alkyl group, a phenyl $C_{1-4}$ alkyl group in which the phenyl group is unsubstituted or substituted by halo, $C_{1-4}$ alkyl or $C_{1-4}$ alkoxy, or $C_{3-4}$ alkenyl; or (c) hydrolysing a compound of formula

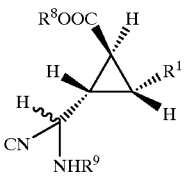

IV in which $R^1$ represents any of the values defined in claim 1, $R^8$ represents a hydrogen atom or a carboxy protecting group, and $R^9$ represents a hydrogen atom or an amine protecting group;

followed when necessary by recovering a diastereomer or isomer of the compound, or forming a salt or ester thereof.

9. A method of treating a patient suffering from or susceptible to a disorder of the central nervous system, which comprises administering an effective amount of a compound of formula I according to claim 1, or a pharmaceutically acceptable metabolically labile ester thereof, or a pharmaceutically acceptable salt thereof.

* * * * *